US006924101B2

(12) United States Patent
Zyskind et al.

(10) Patent No.: US 6,924,101 B2
(45) Date of Patent: Aug. 2, 2005

(54) METHODS FOR IDENTIFYING ANTI-MICROBIAL AGENTS

(75) Inventors: Judith W. Zyskind, La Jolla, CA (US); R. Allyn Forsyth, San Diego, CA (US)

(73) Assignee: San Diego State University Foundation, San Diego, CA (US)

( * ) Notice: Subject to any disclaimer, the term of this patent is extended or adjusted under 35 U.S.C. 154(b) by 129 days.

(21) Appl. No.: 09/805,664

(22) Filed: Mar. 13, 2001

(65) Prior Publication Data

US 2002/0058260 A1 May 16, 2002

Related U.S. Application Data

(62) Division of application No. 08/971,090, filed on Nov. 14, 1997, now Pat. No. 6,228,579.

(51) Int. Cl.$^7$ .......................... C12Q 1/68; C12P 19/34; C07H 21/02

(52) U.S. Cl. .................. 435/6; 435/91.2; 536/23.1; 536/24.3; 436/501; 436/518

(58) Field of Search .................... 435/6, 912; 536/23.1, 536/24.3; 436/518, 501

(56) References Cited

U.S. PATENT DOCUMENTS

| | | | | |
|---|---|---|---|---|
| 4,788,038 A | * | 11/1988 | Matsunaga ................... | 422/22 |
| 4,906,742 A | | 3/1990 | Young et al. ................. | 536/27 |
| 5,217,889 A | | 6/1993 | Roninson et al. | |
| 5,510,240 A | * | 4/1996 | Lam et al. ................... | 435/7.1 |
| 5,639,595 A | * | 6/1997 | Mirabelli et al. .............. | 435/6 |
| 5,665,550 A | | 9/1997 | Roninson et al. | |
| 5,679,523 A | | 10/1997 | Li et al. | |
| 5,811,234 A | * | 9/1998 | Roninson et al. .............. | 435/6 |
| 5,821,076 A | * | 10/1998 | Timberlake et al. .......... | 435/34 |
| 5,955,275 A | * | 9/1999 | Kamb ............................ | 435/6 |
| 6,037,123 A | * | 3/2000 | Benton et al. ................. | 435/6 |
| 6,248,525 B1 | | 6/2001 | Nilsen ........................... | 435/6 |
| 6,303,115 B1 | | 10/2001 | Natsoulis | |

FOREIGN PATENT DOCUMENTS

| | | |
|---|---|---|
| EP | 0 816 511 | 1/1998 |
| EP | 0 837 142 | 4/1998 |
| WO | WO 97/48822 | 12/1997 |
| WO | WO 98/20161 | 5/1998 |
| WO | WO 99/28508 | 6/1999 |
| WO | WO 99/35494 | 7/1999 |
| WO | WO 99/50462 | 10/1999 |
| WO | WO 99/52926 | 10/1999 |
| WO | WO 99/53079 | 10/1999 |

OTHER PUBLICATIONS

Cormier–Regard et al, "Differential display: identifying genes involved in cardiomyocyte proliferation", Mol. Cell. Biochem. 172:111–120, Jul. 1997.*

Gossen et al, "Inducible gene expression systems for higher eukaryotic cells", Current Opinion Biotechnol. 5:516–520, 1994.*

Gossen et al, "Inducible gene expression systems for higher eukaryotic cells", Current Opinion Biotechnol. 5:516–520.*

Kernodle, D.S., et al., "Expression of an Antisense hla Fragment in Staphylococcus aureus Reduces Alpha–Toxin Production*In* Vitro *and Attenuates Lethal Activity in a Murine Model*," Infection and Immunity, vol. 65, No. 1 (1997), pp. 179–184.

Parish, T., et al., "Development and use of a conditional antisense mutagenesis system in mycobacteria," FEMS Microbiology Letters, vol. 154 (1997), pp. 151–157.

Akhtar, S., et al., "In vivo studies with antisense oligonucleotides," Tips, vol. 18, pp. 12–18 (Jan. 1997).

Xie, Y., et al., "A ribozyme–mediated, gene 'knockdown' strategy for the identification of gene function in zebrafish," Proc. Natl. Acad. Sci. USA, vol. 94, pp. 13777–13781 (Dec. 1997).

Spann, T., et al., "Mutagenesis and gene identification in Dictyostelium by shotgun antisense," Proc. Natl. Acad. Sci. USA, vol. 93, pp. 5003–5007 (May 1996).

Li, L., et al., "tsg101: A Novel Tumor Susceptibility Gene Isolated by Controlled Homozygous Functional Knockout of Allelic Loci in Mammalian Cells," Cell, vol. 85, pp. 319–329 (May 3, 1996).

Mao, J., et al., "Gene Regulation by Antisense DNA Produced in Vivo," J. Biol. Chem., vol. 270, No. 34, pp. 19684–19687 (1995).

Ripalti, A., et al., "Cytomegalovirus–Mediated Induction of Antisense mRNA Expression ... Identification of an Essential Gene," J. Virol., vol., 69, No. 4, pp. 2047–2057 (Apr. 1995).

Murphy, C., et al., "A double counter–selection system for the study of null alleles of essential genes in Escherichia coli," Gene, 155, pp. 1–7 (1995).

Inokuchi, Y., et al., "A Hammerhead Ribozyme Inhibits the Proliferation of an RNA Coliphage SP in Escherichia coli," J. Biol. Chem., vol. 269, pp. 11361–11366 (1994).

Diederich, L., et al., "A Versatile Plasmid Vector System for the Regulated Expression of Genes in Escherichia coli," BioTechniques, vol. 16, No. 5, pp. 916–923 (1994).

Jacobs, C., et al., "Bacterial cell wall recycling provides cytosolic muropeptides as effectors for β–lactamase induction," The EMBO Journal, vol. 13, No. 19, pp. 4684–4694 (1994).

(Continued)

Primary Examiner—Jeffrey Fredman
(74) Attorney, Agent, or Firm—Fish & Richardson P.C.

(57) ABSTRACT

A method for identifying endogenous microbial proliferation genes for growth and viability is disclosed herein. The method involves exogenous nucleic acids that are used to conditionally produce antisense inhibitors of endogenous complementary mRNAs in a microorganism. Antisense fragments that result in lethality when expressed indicate that the endogenous gene is a proliferation gene. The method can also be used with sequences in sense orientation. The strategy can be used to identify new gene targets for novel antibiotics.

88 Claims, 12 Drawing Sheets

OTHER PUBLICATIONS

Lindquist, S., et al., "AmpG, a signal transducer in chromosomal β–lactamase induction," *Molecular Microbiology*, 9(4), pp. 703–715 (1993).

Chrisey, L., et al. "Internalization of Oligodeoxyribonucleotides by *Vibrio parahaemolyticus*," *Antisense Research and Development*, 3, pp. 367–381 (1993).

Gasparro, F.P., et al., "Photoactivatable Antisense DNA: Suppression of Ampicillin Resistance in Normally Resistant *Escherchia coli*," *Antisense Research and Development*, 1, pp. 117–140 (1991).

Hastie, N., et al., "Analysis of mRNA populations by cDNA–mRNA hybrid–mediated inhibition of cell–free protein synthesis," *Proc. Natl. Acad. Sci. USA*, vol. 75, No. 3, pp. 1217–1221 (1978).

Genbank Accession No. AF000956.

Genbank Accession No. M20791.

Holzmayer TA, Pestov DG, Roninson IB., Isolation of dominant negative mutants and inhibitory antisense RNA sequences by expression selection of random DNA fragments, *Nucleic Acids Res* Feb. 25, 1992;20(4):711–717.

Gudkov, A. V., and Roninson, I.B., Isolation of Genetic Suppressor Elements (GSEs) from Random Fragment cDNA Libraries in Retroviral Vectors, Methods in Molec. Biol., vol. 69, cDNA Library Protocols, Edited by I.G. Cowell and C.A. Austin, Humana Press, Inc. Totowa, N.Y.

Genbank Accession No. N14029.

Genbank Accession No. s67816.

\* cited by examiner

```
  1  cugcagaagc agaaagaagg uaagaaacgc augaagcaga ucgguaacgu
 51  cgagcugccg caggaagcgu uccucgccau ucugcacguc ggcaaagaca
101  acaaauaacc cuuaggaguu ggcauggcga auuguuugc  ccugauucug
151  gugauugcca cacuggugac gggcauuuua uggugcgugg auaaauucuu
201  uuucgcaccu aaacggcggg aacgucaggc agcggcgcag gcggcucggg
251  acucacugga uaaagcaacg uugaaaaagg uugcgccgaa gccuggcugg
301  cuggaaaccg gugcuucugu uuuuccggua cuggcuaucc cccgucaggu
351  gcguucguuu auuuaugaac cguuccagau uagagaaguu ugcuuauggc
401  cgacucuguu aauggugau  cuaucuacca gaaaacgcug aucgaaaacg
451  auuaaagauc cuaucuacca gaaaacgcug aucgaaaacg gucauccgaa
501  acgcggcgau aucguggucu uuaaauauuc ggaagaucca aagcuu
```

FIG. 1

```
  1  cugcaggcug agugungcc cuacaaaug caacaacgac auggauuaca
 51  acacccucau aaacaaaggg caaucaccug aucuaagcuc uuaccuauga
101  cagugauagg uuaugccuuu uacucgacuu uugcacugac ugaaaaggac
151  aaauuaaugu uaaaaaagau acuuuuacug gcucugcuuc cugcaaucgc
201  cuucgcagag gaacuuccug cuccaguaaa agcgauugaa aaacagggca
251  uuacaaucau caaaacauuc gaugccccg gaggaaugaa agguuaucuc
301  ggaaaguagg aggauauggg cgucaccauc uaccugacuc cagauggaa
351  gcacgcuauc ucugguuaca uguacaacga gaaaggugaa aaccugagua
401  acacacuuau cgaaaaagaa auuuacgcac cuggcucuuc cagccggacg
451  caacggaugg aacaauccca cuggcucuuc gacgguaaaa aagaugcgcc
501  ggucauuguc uacgucuucg ccgauccguu cugcccauau uguaaacagu
551  ucuggcagca ggcgcgcccg ugguuagauu cuggcaaagu gcaauuaaga
601  acauuguugg uugggguuau caagccagaa agcccggcga cagcagcggc
651  aauucuugcc uccaaagauc ccgcaaaauc cuggcaacaa uaugaagccu
701  cuggugcaa gcuu
```

FIG. 2

```
  1  ctgcaggctg aggtgttgcc cttacaaatg caacaaacgac atggattaca
 51  acaccctcat aaacaaaggg caatcacctg atctaagctc ttacctatga
101  cagtgatagg ttatgccttt tactcgactt ttgcactgac tgaaaaggac
151  aaattaatgt taaaaaagat actttactg gctctgcttc ctgcaatcgc
201  cttcgcagag gaacttcctg ctccagtaaa agcgattgaa aaacagggca
251  ttacaatcat caaaacattc gatgcccccg gaggaatgaa aggttatctc
301  ggaaagtatc aggatatggg cgtcaccatc tacctgactc cagatggtaa
351  gcacgctatc tctggttaca tgtacaacga gaaaggtgaa aacctgagta
401  acacacttat cgaaaaagaa atttacgcac ctggctcctc cagccggacg cgaaatgtgg
451  caacggatgg aacaatccca ctggctcctc gacggtaaaa aagatgcgcc
501  ggtcattgtc tacgtcttcg ccgatccgtt ctgcccatat tgtaaacagt
551  tctggcagca ggcgcgcccg tgggtagatt ctggcaaagt gcaattaaga
601  acattgttgg ttggggttat caagccagaa agcccggcgz cagcagcggc
651  aattcttgcc tccaaagatc ccgcaaaaac ctggcaacaz tatgaagcct
701  ctggtggcaa gctt
```

FIG. 3

```
   1  gaauucguac uaccaacugc gagaagcuca uaccugccug acgugccgcc
  51  aucggcacca ggcuguggcu ggucauaccc ggugagguau uggcuuccag
 101  cagauaaaac uguccaucgc uguccagcau aacgucaaua cgucccauc
 151  cuuugcaacc uaacgucguc caugcuuuca gcacuaaugc cugcaaauug
 201  gccucuugug acgcuuccag accugcgggg cagaaauacu gugucucauc
 251  agagagauac uucgccucau aaucauagaa gguuccggac gguugaauac
 301  guauugacgg uaaaauuucu ucaccgagua ucgcaaccgu gaacuccggc
 351  ccacuuagcc auuuuucaau caauacuucu ucaucgugcu gaaaugccaa
 401  ucuuaaugca ucuuguagag cauuuucugc uacuacuuuu gacauuccca
 451  cacuggaacc uucgcggcuc ggcuuaacga uaaccggcaa acccagagca
 501  gaaauuucug cuaacugcuu aucgcucagg ccuuuuucaa acucugcgcg
 551  gguuaacgcu acccacggcg cgaccgguaa accggcaccu ugccauagaa
 601  guuugcugcg uaguuuaucc auugaaagcg cagaugccau cacuccgcuu
 651  ccgguauaag gcaagcccau cagcucgagc auccccugca gcguaccauc
 701  uucaccgccg cgaccgugua gcgcgauaaa cacuuucuga aagcccaucg
 751  acuucaguug cgucacgucg acucuuucg ggucgacagg auacgcguca
 801  auaccgccuu cacgcaguec ggcuaacacc gcugcgccag aaucagaga
 851  aacuucccgc ucagcggagg ucccacccaa caggaccgcg auuuuaucag
 901  ucauguuguu cuuccuccgg aguuugcggc uucaguuuga uuucagcuaa
 951  agaacgggca auuuuuccaa uauuaccagc cccugaacg agaaucaggu
1001  cguuaccggu uaauaccggu gccagcaucu cggcuacccg cgccggaucc
```

FIG. 4

```
  1  gaauucgugg augcuggugu ccugagacau aucagcgaug guaucgguca
 51  gcacacuguu aaccgcaucg gcgauauuuu uguuggaggc cuggaacgca
101  ccuucaacgu uguagcuggc acgauaguuu uugucauuu uguugccauu
151  cugcgcggua gcgaugaugg cgauauccgc uuuggucgcg auguguagc
201  gcacguugcc cuggacacg ucagcauaca guuggcuaac gaugauuugc
251  agauuaaccg ggccauucgg accaaccaug uaaccacgcg cggucaucug
301  uuuuuccagc acuucuugca gcaggaaacg cagaucgcgg gaggcgguca
351  ggguaacgau uugauuaucg cgggugacuu uugccagcgc cugaucggua
401  cgcugaucgg caccauuaau gcuuacgguc acgcccauca ggcuuggauc
451  c
```

FIG. 5

```
  1  ctgcaggctt taatgataag atttgtgcgc taaatacgtt tgaatatgat
 51  cgggatggca ataacgtgag tggaatactg acgcgctggc gacagtttgg
101  taaacgctac ttctggccgc atctcttatt agggatggtt gcggcgagtt
151  taggtttgcc tgcgctcagc aacgccgccg aaccaaacgc gcccgcaaaa
201  gcgacaaccc gcaaccacga gccttcagcc aaagttaact ttggtcaatt
251  ggccttgctg gaagcgaaca cacgccgccc gaattcgaac tattccgttg
301  attactggca tcaacatgcc attcgcacgg taatccgtca tctttctttc
351  gcaatggcac cgcaaacact gcccgttgct gaagaatctt tgcctcttca
401  ggcgcaacat cttgcattac tggatacgct cagcgcgctg ctgacccagg
451  aaggcacgcc gtctgaaaag ggttatcgca ttgattatgc gcatttttacc
501  ccacaagcaa aattcagcac gcccgtctgg ataagccagg cgcaaggcat
551  ccgtgctggc cctcaacgcc tcacctaaca acaataaacc tttacttcat
601  tttattaact ccgcaacgcg gggcgtttga gattttatta tgctaatcaa
651  attgttaact aaagtttttcg gtagtcgtaa cgatcgcacc ctgcgccgga
701  tgcgcaaagt ggtcaacatc atcaatgcca tggaaccgga gatggaaaaa
751  ctctccgacg aagaactgaa agggaaaacc gcagagtttc gtgcacgtct
801  ggaaaaaggc gaagtgctgg aaaatctgat cccgga
```

FIG. 11

```
  1  uccgggauca gauuuccag cacuucgccu uuuuccagac gugcacgaaa
 51  cucugcgguu uucccuuuca guucuucguc ggagaguuuu uccaucuccg
101  guuccauggc auugaugaug uugccacuu ugcgcauccg gcgcagggug
151  cgaucguuac gacuaccgaa aacuuuaguu aacaauuuga uuagcauaau
201  aaaaucucaa acgccccgcg uugcggaguu aauaaaauga aguaaagguu
251  uauuguuguu aggugaggcg uugagggcca gcacggaugc cuugcgccug
301  gcuuauccag acgggcgugc ugaauuuugc uuguggggua aaaugcgcau
351  aaucaaugcg auaacccuuu ucagacggcg ugccuuccug ggucagcagc
401  gcgcugagcg uauccaguaa ugcaagaugu ugcgccugaa gaggcaaaga
451  uucuucagca acgggcagug uuugcggugc cauugcgaaa gaaagaugac
501  ggauuaccgu gcgaauggca uguugaugcc aguaaucaac ggaauaguuc
551  gaaucgggc ggcgugu cgcuuccagc aaggccaauu gaccaaaguu
601  aacuuuggcu gaaggcucgu gguugcgggu ugucgcuuuu gcgggcgcgu
651  uugguucggc ggcguugcug agcgcaggca aaccuaaacu cgccgcaacc
701  aucccuaaua agagaugcgg ccagaaguag cguuuaccaa acugucgcca
751  gcgcgucagu auccacuca cguuauugcc aucccgauca uauucaaacg
801  uauuagcgc acaaaucuua ucauuaaagc cugcag
```

FIG. 12

METHODS FOR IDENTIFYING ANTIMICROBIAL AGENTS

CROSS-REFERENCES TO RELATED APPLICATIONS

The present application is a divisional of and claims the benefit of priority under 35 USC 120 of U.S. application Ser. No. 08/971,090, filed Nov. 14, 1997, issued as U.S. Pat. No. 6,228,579, on May 8, 2001. This application and patent are explicitly incorporated herein by reference in their entirety and for all purposes.

STATEMENT AS TO FEDERALLY SPONSORED RESEARCH

Research reported herein was supported in part by the National Science Foundation and the National Institutes of Health. The United States government may have certain rights in this invention.

BACKGROUND OF THE INVENTION

Genes that encode proteins essential for microbial growth or viability are useful targets for antibiotics because inhibition of such proteins by an antibiotic can reduce or eliminate the spread of infectious disease in a patient. The emergence of bacteria resistant to multiple antibiotics has led to renewed interest in isolating variants of known antibiotics and also in identifying new required genes and the corresponding gene products that could serve as new targets for novel antibiotics.

Approximately fifteen different bacterial proteins encoded by essential genes have been used as targets for antibiotics. Such target proteins include ribosomal proteins, gyrase, RNA polymerase and proteins involved in the synthesis of the peptidoglycan layer and its precursors. However, there are estimated to be more than 4000 putative genes in the genome of the bacterium *Escherichia coli* and it is not known how many of these genes are required for growth and/or viability. The discovery of additional required genes could facilitate the search for new antibiotics.

Microbial genes required or essential for growth and/or viability have been identified by two major techniques. One approach is to determine the nucleotide sequence of the genome of a microbial species of interest. Sequence information is then compared to sequences in computer databases to identify possible functions for the putative gene sequences. To prove that a putative gene identified only by sequence comparisons is in fact an essential gene, however, a null or "knockout" mutation must be made in the gene. It must be shown that a microorganism containing the null mutation cannot survive unless it is complemented by a wild type allele of the gene. Such an approach is time consuming and, in some species, can be difficult.

A second approach is to isolate conditionally lethal mutants by means such as chemical mutagenesis. A common type of conditional lethal mutation is a temperature-sensitive mutation, in which the mutant is non-viable at higher temperature such as 42° C. but is viable at a lower temperature such as 30° C. The mutation is then mapped and identified by cloning and genetic complementation. The mutagenesis techniques employed are sometimes not completely random, thus reducing the likelihood of identifying a required gene that does not have a "hot spot" for the mutagen used. Moreover, products of some required genes may not be amenable to the formation of conditional lethal mutants. Such essential genes would not be identified by this approach.

SUMMARY OF THE INVENTION

The present invention is based on the discovery that microbial genes and their encoded proteins essential for growth and/or viability can be identified by introduction into a microorganism of an exogenous nucleic acid having sequence similarity to the microbial gene. The exogenous nucleic acid can be, for example, an antisense RNA that is derived from a chromosomal fragment cloned downstream of an inducible promoter. The endogenous gene can be identified as required by the inhibition of proliferation of microorganisms containing or expressing the exogenous nucleic acid, compared to the proliferation of microorganisms that do not contain or are not expressing the nucleic acid. The invention facilitates the rapid, efficient identification of microbial genes not previously known to be required for growth or viability.

It will be evident to those skilled in the art that the invention can be applied to any organism for which it is feasible to 1) isolate and fragment the chromosome of the organism, 2) re-introduce exogenous nucleic acid fragments of the organism or fragments substantially similar to those of the organism back into the organism and 3) culture the organism without the exogenously added nucleic acids.

The present invention advantageously permits the rapid, inexpensive identification of microbial genes that heretofore have not been identified as required for survival. The method comprises the steps of introducing an exogenous nucleic acid into a microorganism and determining the proliferation of the microorganism relative to the proliferation of the microorganism when the exogenous nucleic acid is not present or not expressed. The exogenous nucleic acid has substantial sequence identity to an endogenous microbial gene. The exogenous nucleic acid can be operably linked to a regulatory element effective for controlling expression of the nucleic acid, either in sense orientation or in antisense orientation to the regulatory element. The regulatory element can control expression via chemical induction of the exogenous nucleic acid. The microorganism can be, for example, a bacterium, either gram-negative or gram-positive, a fungus, or an Archaebacteria.

The novel genes and the proteins encoded by such genes are promising targets for new antimicrobial agents. A method for identifying such agents comprises the steps of contacting an agent with a microorganism having a proliferation gene and determining the effect of the agent on the proliferation gene or a product of the proliferation gene. The proliferation gene can be endogenous to the microorganism, or can be from another source microorganism. The effect of the agent on the proliferation gene can be, for example, on transcription or on translation of the proliferation gene.

Specific genes and their mRNAs identified by the novel method can be targets for antisense polynucleotide inhibitors, and these antisense polynucleotides can have therapeutic value. A method for inhibiting expression of a microbial proliferation gene comprises contacting a microorganism having a proliferation gene with an antisense polynucleotide having substantial sequence identity to the proliferation gene.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

FIG. 1 shows the nucleotide sequence of an antisense RNA to *E. coli* lepB mRNA, expressed from the DNA insert in plasmid pJB37 (SEQ ID NO: 3).

FIG. 2 shows the nucleotide sequence of an antisense RNA to *E. coli* viaA mRNA, expressed from the DNA insert in plasmid Pjb53 (SEQ ID NO: 4).

FIG. 3 shows the nucleotide sequence of a 714 nucleotide PstI-HindIII fragment of the *E. coli* viaA gene cloned in pJB53 (SEQ ID NO: 5).

FIG. 4 shows the nucleotide sequence of an antisense RNA to *E. coli* ddlB mRNA, expressed from the DNA insert in plasmid pJB57 (SEQ ID NO: 6).

FIG. 5 shows the nucleotide sequence of an antisense RNA to orf1 of the *E. coli* ampG operon, expressed from the DNA insert in plasmid pJB59 (SEQ ID NO: 7).

FIG. 11 shows the nucleotide sequetice of an 836 nucleotide PstI/HindIII fragment of the *E. coli* secA gene cloned in pJB3 (SEQ ID NO: 8).

FIG. 12 shows the nucleotide sequence of anantisense RNA complementary to *E. coli* secA mRNA (SEQ ID NO: 9).

DESCRIPTION OF THE PREFERRED EMBODIMENTS

Figure 6:
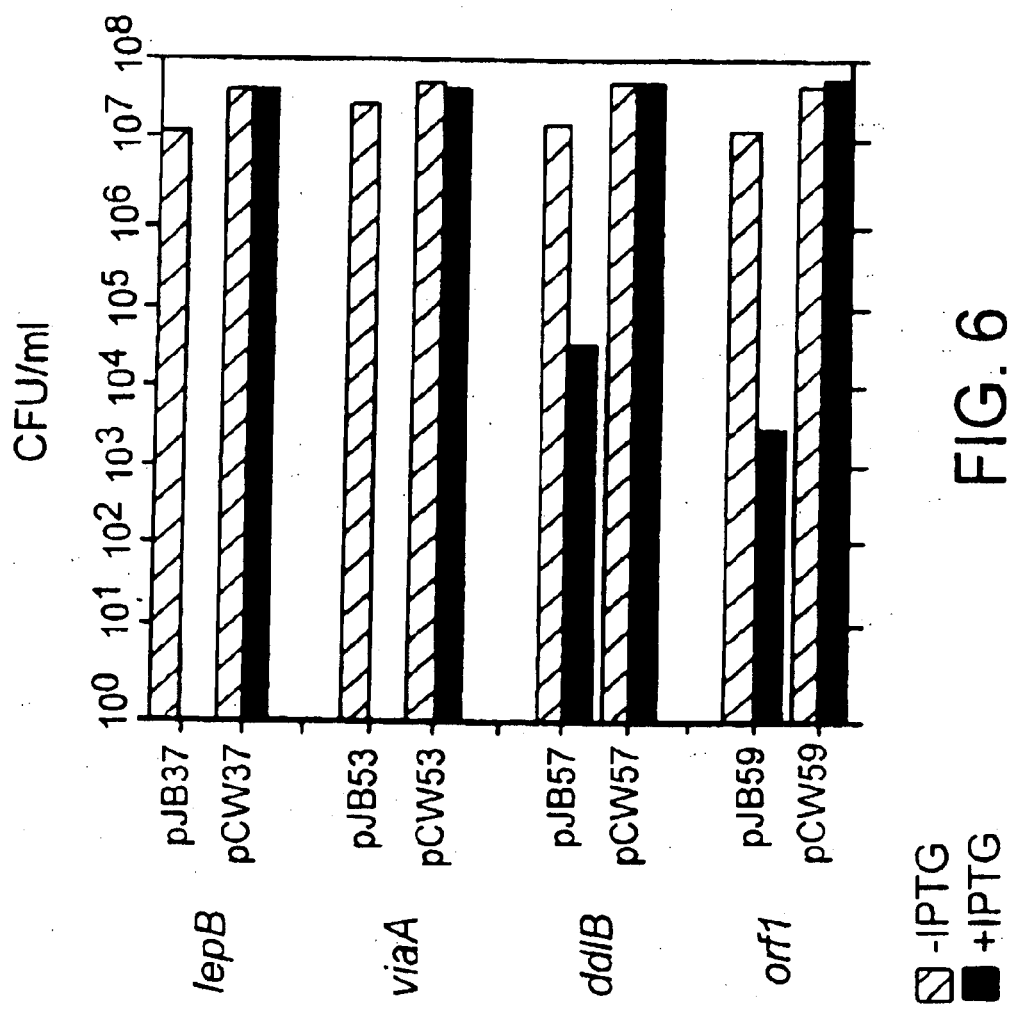
FIG. 6 is a bar graph showing the effect of inducing lepB, ddlB, viaA or orf1 antisense RNA expression on colony formation in *E. coli* DH5α. Striped bars indicate colony forming units (CFUs) per ml of culture for strains grown on semi-solid media in the absence of the inducer IPTG. Solid bars indicate CFUs/ml for strains grown in the presence of IPTG.

The present invention provides an efficient strategy for identifying microbial proliferation genes. Proliferation genes are genes that are necessary for proliferation, i.e., in the absence of gene transcript and/or gene product, growth or viability of the microorganism is reduced or eliminated.

Microorganisms can be used in the invention as a pure culture or may be used as a mixed culture, i.e., more than one strain or species may be used in the novel method. Microorganisms suitable for use in the method include both prokaryotes, and eukaryotes. Bacterial species suitable for use in the method include substantially all bacterial species, both animal and plant pathogenic species, as well as non-pathogenic species. Preferred species are pathogens of mammals, especially pathogens of humans such as *Staphylococcus aureus*.

Either gram-negative and gram-positive bacterial species can be used, e.g., gram-positive *Enterococcus, Bacteriodes, Clostridium* and *Staphylococcus* species and gram-negative *Escherichia, Pseudomonas, Haemophilus, Enterobacter, Vibrio, Salmonella, Helicobacter* and *Moraxella* species. *Mycobacterium* species such as *Mycobacterium tuberculosis* are also suitable for use in the method disclosed herein. Eukaryotic microbes suitable for use in the method include, without limitation, *Cryptococcus neoformans, Nocardia* spp., *Coccidiodes immitis, Toxoplasma* spp., *Leishmania* spp., *Pneumocystis, Trypanosoma* spp., *Giardia* spp., *Plasmodia* spp. (e.g., *Plasmodium falciparium*), *Histoplasma capsulatum*, and *Candida albicans*.

The novel method for identifying microbial proliferation genes comprises the step of introducing an exogenous nucleic acid into a microorganism. The exogenous nucleic acid may be obtained, for example, from a restriction digest of total genomic (e.g. chromosomal and episomal) DNA from a microorganism of interest, or from total genomic DNA that has been subjected to physical shear. Sheared DNA may result in a more random set of fragments than would otherwise be generated by restriction digestion. Nucleic acid fragments obtained by partial or total restriction digestion or by shearing can be size selected by agarose gel electrophoresis or sucrose gradients, if desired. Exogenous nucleic acid can also be obtained by chemical synthesis (synthetic DNA having a random sequence or synthetic DNA based on information in a nucleic acid sequence database), from a cDNA library, or by other means known to the art.

An exogenous nucleic acid of the present invention can be in the form of RNA or in the form of DNA, including cDNA, synthetic DNA or genomic DNA. The DNA can be double-stranded or single-stranded and, if single-stranded, can be either a coding strand or non-coding strand. RNA can be, for example, mRNA or a combination of ribo- and deoxyribo-nucleotides.

An exogenous nucleic acid of the present invention has substantial sequence identity to an endogenous microbial proliferation gene. It should be appreciated, however, that it is not necessary to have prior knowledge of sequence identity to an endogenous gene. In fact, an advantage of the present method is that a plurality of randomly generated nucleic acid fragments, whose identity to particular endogenous genes has not been determined, can be screened to identify a fragment (or fragments) that inhibit microbial proliferation. The relationship between such a fragment and the endogenous microbial gene can then be determined.

An exogenous nucleic acid has at least about 70% sequence identity, preferably at least about 80% sequence identity, more preferably at least about 90% sequence identity to the endogenous microbial proliferation gene. Sequence identity can be determined, for example, by computer programs designed to perform single and multiple sequence alignments. Nucleic acids having at least about 70% nucleotide sequence identity to the endogenous gene can also be identified by their ability to hybridize to the endogenous gene under conditions of moderate stringency. Nucleic acids having at least about 80% sequence identity, or at least about 90% sequence identity, or at least about 95% sequence identity to the endogenous gene can hybridize under high stringency conditions.

Hybridization can be measured by Southern analysis (Southern blotting), a method by which the presence of DNA sequences in a target nucleic acid mixture are identified by hybridization to a labeled oligonucleotide or DNA fragment probe. Southern analysis typically involves electrophoretic separation of DNA digests on agarose gels, denaturation of the DNA after electrophoretic separation, and transfer of the DNA to nitrocellulose, nylon, or another suitable membrane support for analysis with a radiolabeled, biotinylated, or enzyme-labeled nucleic acid as described in sections 9.37–9.52 of Sambrook et al., *MOLECULAR CLONING: A Laboratory Manual*, Vol. 2, Chapter 11, Cold Spring Harbor Laboratory Press, Cold Spring Harbor, N.Y. (1989).

An exogenous nucleic acid can hybridize to the endogenous gene under moderate stringency conditions or under high stringency conditions. High stringency conditions are used to identify nucleic acids that have a high degree of homology or sequence identity to one another. High stringency conditions can include the use of a denaturing agent such as formamide during hybridization, e.g., 50% formamide with 0.1% bovine serum albumin/0.1% Ficoll/0.1% polyvinylpyrrolidone/50 mM sodium phosphate buffer at pH 6.5 with 750 mM NaCl, and 75 mM sodium citrate at 42° C. Another example is the use of 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C., with washes at 42° C. in 0.2×SSC and 0.1% SDS. Alternatively, low ionic strength and high temperature can be employed for washing, for example, 0.015 M NaCl/0.0015 M sodium citrate (0.1× SSC); 0.1% sodium lauryl sulfate (SDS) at 65° C.

Moderate stringency conditions are hybridization conditions used to identify nucleic acids that have less homology or identity to one another than do nucleic acids identified under high stringency conditions. Moderate stringency conditions can include the use of higher ionic strength and/or lower temperatures for washing of the hybridization membrane, compared to the ionic strength and temperatures used for high stringency hybridization. For example, a wash solution comprising 0.060 M NaCl/0.0060 M sodium citrate (4× SSC) and 0.1% sodium lauryl sulfate (SDS) can be used at 50° C., with a last wash in 1× SSC, at 65° C. Alternatively, a hybridization wash in 1×SSC at 37° C. can be used.

Hybridization can also be done by Northern analysis (Northern blotting), a method used to identify RNAs that hybridize to the nucleic acid used as the probe. The probe is labeled with a radioisotope such as $^{32}P$, by biotinylation, or with an enzyme. The RNA to be analyzed can be electrophoretically separated on an agarose or polyacrylamide gel, transferred to nitrocellulose, nylon, or other suitable membrane, and hybridized with the probe, using standard techniques well known in the art such as those described in sections 7.39–7.52 of Sambrook et al., supra.

The exogenous nucleic acid can be less than about 400 nucleotides in length, e.g., from about 10 to about 400 nucleotides in length. An exogenous nucleic acid can also be greater than about 400 nucleotides in length, e.g., from about 10 to about 5,000 nucleotides in length. It is generally preferred that an exogenous nucleic acid of about 15 to about 1,500 nucleotides in length be used in the method, e.g., at least about 15 nucleotides, or at least about 30 nucleotides, or at least about 100 nucleotides.

In some embodiments, the nucleotide sequence of the exogenous nucleic acid has substantial complementarity to the coding sequence of the endogenous microbial proliferation gene, as in an antisense RNA. In other embodiments, the nucleotide sequence of the exogenous nucleic acid is the same as or substantially similar to the coding strand sequence of the endogenous gene, e.g., is a sense RNA. An exogenous nucleic acid preferably exerts a microbiostatic (e.g., bacteriostatic or fungistatic) or microbiocidal (e.g., bacteriocidal or fungicidal) effect by antisense inhibition of a microbial proliferation gene. For example, an exogenous nucleic acid can be DNA that is transcribed into an RNA molecule complementary (antisense) to mRNA produced by the endogenous microbial gene. In such an embodiment, the exogenous nucleic acid is the DNA. The expressed antisense RNA has the capability to inhibit translation of the mRNA and thereby inhibit the proliferation of the microbial cells.

There are several possible modes of action for antisense molecules. For example, the Shine Dalgarno sequence and start codon of a bacterial proliferation gene mRNA could be targeted by an antisense nucleic acid, and thereby inhibit ribosomal loading onto the mRNA. Alternatively, a hybrid molecule could be formed between an antisense nucleic acid and a portion of the coding region of the microbial proliferation gene mRNA. In this case, the mechanism of antisense inhibition could be premature translational termination, due to inhibition of ribosome movement or decreased mRNA stability. As another alternative, a hybrid could be formed between an antisense nucleic acid and a portion of the microbial proliferation gene mRNA near the transcriptional terminator. In addition, a triple helix could form between the proliferation gene and the exogenous nucleic acid, thereby inhibiting transcription of the proliferation gene. In some instances, it is possible that more than one of the above mechanisms, or a different mechanism, may be responsible for the effect on proliferation. The present invention encompasses these and other mechanisms.

Alternatively, an exogenous nucleic acid exerts a microbiostatic or microbiocidal effect by sense inhibition of a microbial proliferation gene, i.e., dominant negative suppression. For example, an exogenous nucleic acid can be DNA that is transcribed into an RNA molecule having a sequence substantially identical to mRNA produced by the endogenous microbial gene. The expressed sense RNA has the capability to inhibit the proliferation of the microbial cells, possibly by producing proteins or truncated peptides that interfere with normal function of the endogenous proliferation gene product.

As discussed herein, it is preferable to obtain a plurality of exogenous nucleic acids, e.g., a library of restriction fragments of a microbial genome. Such a population of exogenous nucleic acids has substantial sequence identity to a large number of endogenous microbial genes, preferably the entire genome. The population is screened in parallel for an effect on microbial proliferation; those fragments exerting an inhibitory effect on growth and/or viability are selected for further study.

Typically, an exogenous nucleic acid is introduced into a microorganism on a vector, e.g. a plasmid or phage vector. Illustrative examples of vectors are the pLEX series of plasmids described in Diederich, L. et al., Biotechniques 16:916–923 (1994). Other suitable vectors are known in the art. If desired, assays can be used to confirm that the exogenous nucleic acid has been effectively introduced in order to confirm that the antiproliferative effect is due to the exogenous nucleic acid and not due to some other factor.

Techniques are known in the art for the introduction of exogenous nucleic acid into microorganisms, e.g., gram-negative as well as gram-positive bacteria. Techniques for introducing exogenous nucleic acid include, without limitation, lambda phage in vitro packaging, freeze-thaw mediated transformation, $CaCl_2$-mediated transformation, liposomes, electroporation, natural transformation, conjugation and particle gun transformation.

An exogenous nucleic acid preferably is operably linked to at least one suitable regulatory sequence to facilitate expression of the exogenous nucleic acid. Regulatory sequences typically do not themselves code for a gene product. Instead, regulatory sequences control the expression level of the exogenous nucleic acid. An exogenous nucleic acid can be operably linked to a suitable inducible regulatory sequence in antisense orientation or in sense orientation.

Examples of regulatory sequences are known in the art and include, without limitation, promoters induced in response to chemical inducers, promoters induced in response to environmental changes (temperature shifts, radiation and the like) and promoters repressed in response to the presence of chemical agents. Examples of promoters induced in the presence of chemical inducers include the *E. coli* lac promoter (induced with isopropyl-β-D-thiogalactopyranoside, also known as IPTG), the tet promoter (induced with tetracycline) and the hybrid tac promoter (induced with IPTG). Examples of promoters repressed in response to a chemical repressor include the trp promoter (repressed by typtophan, a corepressor). Other suitable regulatory sequences may be included if desired. For example, the rrnB transcriptional terminator 3' non-coding region, rrnBtlt2 may be used.

Molecular biology techniques for linking an exogenous nucleic acid to a regulatory sequence effective for controlling expression of the nucleic acid are known in the art. In some embodiments, more than one regulatory element is operably linked to the exogenous nucleic acid, provided that the nucleic acid can be expressed when desired.

The novel method also includes the step of determining the effect of the exogenous nucleic acid on microbial proliferation, relative to the effect in the absence of the exogenous nucleic acid. For example, the exogenous nucleic acid can be operably linked to an inducible promoter and the effect on proliferation can be measured after induction of expression. The effect on proliferation is compared to microbial proliferation when the nucleic acid is not induced and expressed. Means for determining the effect on proliferation include, for example, measuring colony-forming units (CFU), measuring light scattering (optical density), measuring the number of microorganisms in a particle counter, measuring respiratory activity, measuring fluorescence of cell cultures or individual cells after addition of fluorescent dyes and measuring incorporation of precursors to macromolecular (RNA, DNA, protein, cell wall) synthesis, measuring uptake of metabolites and measuring transport.

Typically, microbial cells are cultured for a period of time to allow the exogenous nucleic acid to inhibit endogenous gene expression. Culturing may occur on solid media or in liquid media, on complex media or minimal media. Culturing may be carried out during an exponential growth phase, stationary growth phase, or during a stress phase. Nevertheless, it should be appreciated that the effect on proliferation can be determined without culturing the microorganism. For example, inhibition of a proliferation gene can be identified by a rapid effect on respiratory activity, a measurement that can be carried out under conditions that do not support long-term growth and viability. Techniques for determining the effect on proliferation that do not involve culturing of microorganisms are within the scope of the present invention.

Inhibition of bacterial growth is readily determined by comparative or replica plating. Bacteria are plated on solid media under conditions in which there is no production or expression of exogenous nucleic acid. Bacterial colonies are subsequently replica plated to a second plate of solid media under conditions in which production or expression of exogenous nucleic acid occurs. Clones that cannot grow in the presence of exogenous nucleic acid are chosen from the first plate for identification.

Culturing may occur for a period of time appropriate for the strain or species being tested. For example, about a 3 hour delay may occur before growth inhibition is observable with an antisense mechanism. Expressed antisense RNA must bind to and inhibit translation of its chromosomally encoded mRNA counterpart. Reduction in protein gene product may be detectable after 1 hour, but even if translational inhibition were 100% it may take several generations to "dilute out" the active gene product below levels required for viability.

It is often preferable to measure the effect on proliferation under culture conditions similar to those in which it is desired to determine the requirement for the endogenous gene. For example, proliferation genes in a microbial human pathogen are preferably identified under conditions that relate to those found when the pathogen has infected a human, because genes required under such conditions are generally of more interest. It can be useful in some instances to identify proliferation genes under more than one set of conditions, i.e., to determine if the gene is conditionally required. However, the most useful microbial proliferation genes are those genes necessary for growth and/or viability under substantially all conditions, because protein products of such genes are more desirable as targets for novel antibiotics.

Proliferation genes are often highly conserved among different species, for example, different bacterial species. Thus, microbial genes that have been identified as proliferation genes in one species or strain by the method disclosed herein can be used to search for related genes in other species or strains.

In some embodiments, an exogenous nucleic acid is not introduced on a vector (e.g., a plasmid or phage vector), but is introduced as a non-replicating polynucleotide in an amount sufficient to exert an effect on the corresponding endogenous gene without the need for amplification of the amount in vivo. Such exogenous nucleic acids typically are antisense polynucleotides, including both short RNA oligonucleotides, typically 10–50 nucleotides in length, as well as longer RNA fragments that may exceed the length of the endogenous microbial gene itself. Antisense nucleic acids useful for the present invention are substantially complementary to regions of the corresponding proliferation gene mRNA. Hybridization of antisense nucleic acids to their target transcripts can be highly specific as a result of complementary base pairing. The capability of antisense nucleic acids to hybridize is affected by such parameters as length, chemical modification and secondary structure of the transcript which can influence nucleic acid access to the target site. An antisense polynucleotide can also be a DNA segment that synthesizes an antisense RNA inside the cell.

In selecting the preferred length for a given nucleic acid, a balance must be struck to gain the most favorable characteristics. Shorter nucleic acids such as 10-to 15-mers, while offering higher cell penetration, have lower gene specificity. In contrast, while longer nucleic acids of 20–30 bases offer better specificity, they show decreased uptake kinetics into cells. See Stein et al., "PHOSPHOROTHIOATE OLIGODEOXYNUCLEOTIDE ANALOGUES" in *Oligodeoxynucleotides—Antisense Inhibitors of Gene Expression*, Cohen, Ed. McMillan Press, London (1988).

The present invention encompasses both oligomeric nucleic acid moieties of the type found in nature, such as the deoxyribonucleotide and ribonucleotide structures of DNA and RNA. The invention also encompasses synthetic, modified analogues that are capable of binding to an endogenous microbial gene or its mRNA.

In some embodiments, therefore, an antisense polynucleotide of the present invention is a phosphorothioate or methyl phosphonate-linked analogue, which can be nuclease-resistant and thus have increased stability. Alternatively, an antisense polynucleotide can be a peptide nucleic acid, which can be nuclease-resistant and have high affinity for a complementary strand. See, e.g., U.S. Pat. Nos. 5,539,082 and 5,539,083. Nucleic acids can also have adducts that permit cross-linking between strands of an antisense or sense hybrid. Persons of ordinary skill in this art will be able to select other linkages for use in the invention. These modifications also may be designed to improve the cellular uptake and stability of the nucleic acids.

Phosphorothioate modified DNA nucleic acids typically are synthesized on automated DNA synthesizers available from a variety of manufacturers, e.g., available from Perkin-Elmer/Applied Biosystems (Foster City, Calif.). These instruments are capable of synthesizing nanomole amounts of nucleic acids as long as 100 nucleotides. Shorter nucleic acids synthesized by modern instruments are often suitable for use without further purification. If necessary, nucleic acids may be purified by polyacrylamide gel electrophoresis or reverse phase chromatography. See Sambrook et al, *MOLECULAR CLONING: A Laboratory Manual*, Vol. 2, Chapter 11, Cold Spring Harbor Laboratory Press, Cold Spring Harbor, N.Y. (1989).

Illustrative embodiments of antisense polynucleotides includes polynucleotides having substantial sequence complementarity to the *E. coli* lepB, viaA, ddlB, orf1, and secA mRNAs, as well as oligonucleotide subfragments thereof, e.g., about 10 to about 100 nucleotides in length, or about 10 to about 60 nucleotides in length, or about 20 to about 50 nucleotides in length. A desired antisense oligonucleotide can be readily identified by preparing and testing overlapping portions of, e.g., an RNA of FIG. 1, 2, 4–5 or 12 for antiproliferative effects as described herein. For example, antisense oligonucleotides about 30 nucleotides in length, each having a 10 nucleotide overlap with adjacent oligonucleotides, can be synthesized and tested for antiproliferative effects. Those oligonucleotides having such an effect are useful as antiproliferative agents as described herein.

Once a microbial proliferation gene has been discovered, the invention provides a method for identifying an antimicrobial agent targeted at the novel gene or gene product. The method includes the step of contacting an agent to be tested for its antimicrobial properties with a microorganism having a proliferation gene. The proliferation gene present in the microorganism may be a gene endogenous to the microorganism. Alternatively, the proliferation gene can be one that has been introduced from a second microorganism. For example, a proliferation gene from a species for which it is more difficult to evaluate an agent can be introduced into a species for which it is less difficult to evaluate an agent, in order to facilitate testing of various agents.

Contacting includes conditions which allow the test agent to exert an effect, if any, on microbial proliferation, and can occur either in solution or in solid phase. In preferred embodiments, a plurality of agents are tested, e.g. a combinatorial library can be used for screening. The agent is determined to be an antimicrobial agent when the agent is found to exert an effect on a microbial proliferation gene, its mRNA, or its encoded protein as described herein.

The novel screening method is useful for identifying new classes of antimicrobial agents directed at the endogenous microbial proliferation protein targets identified as described herein. Agents suitable for use in the method include inorganic chemical compounds, organic chemical compounds, peptidomimetics, and biologic compounds such as peptides, polypeptides, oligonucleotides and polynucleotides. Typically, the method is useful for identifying an agent that is itself microbiostatic or microbiocidal, e.g., is potentially useful as an antibiotic. In some instances, an agent is useful for identifying a class of structurally related agents that will have efficacious microbiostatic or microbiocidal properties.

If desired, indirect means may be used to determine the effect of an agent on microbial proliferation. For example, an agent can be tested for its effect on enzyme activity if the proliferation gene encodes or is suspected of encoding an enzyme. If a protein does not have an easily assayable enzymatic activity, immunoassays can be carried out with antibody raised against a polypeptide or peptide product of a microbial proliferation gene, in order to identify effects on transcription and translation of the endogenous gene. Northern blots or in vitro transcription assays can be used to determine the effect of the agent on transcription of the microbial proliferation gene. Such assays can be carried out on viable cells, on crude cell lysates or even on purified preparations of the endogenous gene, mRNA or gene product. In addition, structural bioinformatics can be used to identify putative inhibitors and likely mechanisms by which an agent exerts its microbiostatic or microbiocidal effect.

Agents identified by the method can be further evaluated by any method usually applied to the determine the efficacy and pharmacological activity of an antimicrobial agent.

Once a gene has been identified as a proliferation gene, it can be further characterized. Some identified genes will have been previously known as proliferation genes. Others, although having been previously sequenced, will not have been identified as proliferation genes. Others, although having been previously sequenced, are tentatively identified as proliferation genes based on sequence homology to an proliferation gene from another organism. Still others will not have been previously identified or characterized and can be cloned, if desired, using known techniques such as polymerase chain reaction (PCR) technology. See, e.g., U.S. Pat. No. 4,683,195, and subsequent modifications of the procedure described therein. Such genes can also be sequenced by known techniques such as dideoxy sequencing; open reading frames (ORFs) and putative regulatory elements assigned to various regions of the sequenced gene. Homology searches of nucleic acid and protein databases, such as the GenBank, EMBL, and Swiss Prot databases, are useful for deducing possible biochemical and metabolic functions of genes identified as required by the method disclosed herein.

Illustrative examples of proliferation genes include, for example, genes having substantial sequence identity to the *E. coli* viaA gene, the *E. coli* secA gene, the *E. coli* orf1 gene, the *E. coli* ddlB gene and the *E. coli* lepB gene. Such genes can be identified as proliferation genes by sense or antisense inhibition.

In some cases, genes are identified as proliferation genes based on the effect observed with sense constructs. For example, genes having substantial sequence identity to the *E. coli* ugpB gene and a gene having homology to the *E. coli* fimF and fimD genes can be considered proliferation genes because bacterial growth and/or viability is reduced or eliminated when a sense construct to such genes is expressed. Bacterial inhibition by antisense constructs would not ordinarily be expected to occur for such genes. Nevertheless, it should be appreciated that sense constructs that result in bacterial inhibition can be useful to derive antiproliferative agents. For example, peptides useful as antibiotics can be obtained, based on peptides made by the sense construct. Alternatively, nucleic acids useful as antibiotics can obtained based on the RNA made by the sense construct.

All publications, patent applications, patents, and other references mentioned herein are incorporated by reference in their entirety. In addition, the materials, methods, and examples are illustrative only and not intended to be limiting.

EXAMPLES

The following examples use many techniques well-known and accessible to those skilled in the art. Enzymes are obtained from commercial sources and are used according to the vendors' recommendations or other variations known to the art. Abbreviations and nomenclature are employed as commonly used in professional journals such as those cited herein.

Example 1

Generation of E. coli Chromosomal Library

Bacterial strains, plasmids and media. Luria Broth was made as previously described (Sambrook et al., 1989). M9 media (Sambrook et al., 1989) was supplemented with 0.5% casamino acids and 0.2% glucose. Antibiotics were used at the following concentrations in plates and broth: ampicillin, 100 µg/ml; spectinomycin, 100 µg/ml. Isopropyl-β-D-thiogalacto-pyranoside (IPTG) was used at 100 µM or at 1 mM as indicated.

Isolation and cloning of exogenous nucleic acid. E. coli chromosomal DNA was digested with either PstI and HindIII or EcoRI and BamHI and ligated into the vector pLEX5BA, cut with the same enzymes (Diederich et al, Biotechniques 16:916–923 (1994)). Plasmid pLEX5BA contains: I) a Bujard promoter that has binding sites for lac repressor centered at −22 and +11 relative to the start of transcription, ii) a multiple cloning site downstream of the promoter, and iii) an rrnBtlt2 transcriptional terminator after the multiple cloning site. Expression of fragments cloned downstream of the Bujard promoter can be induced with IPTG.

The double digestions were chosen to give fragments with a median length of 2–3 kb (Churchill et al., 1990). The ligation mix was transformed into E. coli DH5α and transformants were selected on plates containing ampicillin. Colonies that grew on ampicillin were subsequently replica plated by physical transfer to a second ampicillin plate containing the inducing agent IPTG at a concentration of 100 µM. Colonies that did not grow in the presence of IPTG were chosen for further characterization.

Inhibition of bacterial growth after IPTG induction. Growth curves were carried out by back diluting cultures 1:20 into fresh media with or without 1 mM IPTG and measuring the $OD_{450}$ every 30 minutes (min). To study transcriptional induction in exponential phase, cultures were diluted 1:10$^6$ or as indicated. The viability (CFU/ml) was determined over time by plating aliquots of the culture on agar with or without IPTG.

There were 53 clones whose proliferation was inhibited after IPTG induction, out of approximately 50,000 PstI-HindIII clones screened. Out of 16,000 EcoRI-BamHI cloned fragments, the growth of 15 transformants was inhibited after IPTG induction. Thus, approximately 0.1% of the inserts resulted in IPTG sensitivity when expressed from the Bujard promoter.

Plasmids pJB1 through pJB68 were cut with restriction enzymes to release the cloned inserts. Sizes ranged from 450 bp to 6 KB. Clones that had inhibition of colony formation after induction with 100 mM IPTG and had inserts less than 1050 bp were selected for further study. Certain plasmid derivatives and strains are listed in Table 1.

The nucleotide sequences of 11 inserts were determined, using plasmid DNA isolated by the method of Zyskind and Bernstein (1992). The primers used for sequencing the inserts were 5' TGTTTTATCAGACCGCTT 3' (SEQ ID NO: 1) and 5' ACAATTTCACAC AGCCTC 3' (SEQ ID NO: 2). These sequences flank the polylinker in pLEX5BA.

The sequences for the 11 chromosomal inserts were analyzed for similarity to sequences in GenBank using BLAST (Altschul, 1990). The presence of open reading frames and ribosome binding sites were scanned using the Genetics Computer Group programs FRAMES and CODONPREFERENCE, at default settings. Clones were designated as "antisense" if the cloned fragment was oriented to the promoter such that the RNA transcript produced appeared complementary to the mRNA from a chromosomal locus. Clones were designated as "sense" if they coded for an RNA fragment that was identical to a portion of the wild type mRNA from a chromosomal locus. About 1/13,000 clones produced an inhibitory antisense RNA.

TABLE 1

E. coli K-12 strains (all F−) and plasmids

| Strain | Genotype/phenotype |
|---|---|
| DH5α | supE44 ΔlacU169(φ80lacZΔM15) hsdR17 recA1 endA1 gyrA96 thi-1 relA1 |
| JRG58201 | Δ(nadC-ampD-ampE-aroP) ampG::kan |

| Plasmids | Vector/Insert |
|---|---|
| pLEX5BA | Ap$^r$ cloning vector |
| pJB3 | pLEX5BA with an 836 bp PstI/HindIII fragment of secA in sense orientation |
| pJB37 | pLEX5BA with a 546 bp PstI/HindIII fragment of lepB in antisense orientation |
| pJB53 | pLEX5BA with a 714 bp PstI/HindIII fragment of viaA in antisense orientation |
| pJB57 | pLEX5BA with a 1050 bp EcoRI/BamHI fragment of ddlB in antisense orientation |
| pJB58 | pLEX5BA with a 783 bp EcoRI/BamHI fragment with homology to fimF and fimD |
| pJB59 | pLEX5BA with a 451 bp EcoRI/BamHI fragment of orfl/ampG in antisense orientation |
| pJB60 | pLEX5BA with a 619 bp EcoRI/BamHI fragment of ugpB in sense orientation |
| pCW37 | pLEX5BA with a 546 bp PstI/HindIII fragment of lepB in sense orientation |
| pCW53 | pLEX5BA with a 714 bp PstI/HindIII fragment of viaA in sense orientation |
| pCW57 | pLEX5BA with a 1050 bp EcoRI/BamHI fragment of ddlB in sense orientation |
| pCW59 | pLEX5BA with a 451 bp EcoRI/BamHI fragment of orfl/ampG in sense orientation |
| pAFΩ | Sp$^r$,St$^r$ derivative of pLEX5BA containing 2 kb SmaI Ω fragment cloned into ClaI site |
| pAF37 | pAFΩ with a 546 bp PstI/HindIII fragment of lepB in antisense orientation |

TABLE 1-continued

E. coli K-12 strains (all F⁻) and plasmids

| | |
|---|---|
| pAF53 | pAFΩ with a 714 bp PstRI/HindIII fragment of ddlB in antisense orientation |
| pAF57 | pAFΩ with a 1050 bp EcoRI/BamHI fragment of viaA in antisense orientation |
| pAF59 | pAFΩ with a 451 bp EcoRI/BamHI fragment of orf1/ampG in antisense orientation |

Example 2

Identification of Proliferation Genes by Antisense Inhibition

Seven clones obtained as described in Example 1 inhibited bacterial proliferation and contained gene fragments in an antisense orientation.

Three of the clones contained fragments of the lepB gene; pJB12, pJB37 and pJB40. pJB37 contains a 546 bp HindIII-PstI insert that expresses an RNA complementary to the carboxy terminal half of the lepB mRNA. The RNA sequence is shown in FIG. 1. LepB encodes the leader peptidase responsible for proteolytic cleavage of the signal peptide from preproteins. Leader peptidase is required for viability and a temperature sensitive lepB mutant lyses at the nonpermissive temperature.

A fragment of an uncharacterized ORF was cloned twice in antisense orientation in pJB39 and pJB53. The antisense clone pJB53 contains a 714 bp PstI-HindIII fragment of this putative ORF, designated herein as viaA (viability inhibited by antisense) and expresses an RNA that is complementary to the putative sense RNA. The sequence of the antisense RNA is shown in FIG. 2 and the sequence of the DNA insert is shown in FIG. 3.

One antisense clone, pJB57, contained a fragment of the ddlB gene. The D-alanyl:D-alanine ligase antisense clone, pJB57, contains a 1050 bp EcoRI-BamHI fragment (with an internal Eco R1 site) that expresses an RNA antisense to the carboxy terminal portion of murC and the first 600 bases of ddlB including its start codon. The RNA sequence is shown in FIG. 4. The product of the ddlB gene, the D-alanyl:D-alanine ligase, ligates 2 D-alanines together which are destined to form part of the peptidoglycan layer. A temperature sensitive ddlB mutant could only grow for 40 min at the non-permissive temperature before lysing, presumably due to the compromised peptidoglycan layer. Lugtenberg E. and van Schijndel-van Dam, A., J. Bact. 113:96–104 (1973). There is a naturally occurring inhibitor of D-alanyl:D-alanine ligase activity, the antibiotic cycloserine.

The ampG operon antisense clone pJB59 contains a 451 bp EcoRI-BamHI fragment which expresses an RNA antisense to a polycistronic mRNA containing orf1 and ampG. The antisense RNA ends 64 nucleotides upstream of the ampG coding region. The orf1 gene product has no known function but has been thought to be dispensable. AmpG forms a cytoplasmic membrane pore through which peptidoglycan subunits are translocated to signal inducible β-lactamase promoters when peptidoglycan damage occurs from β-lactam antibiotics. Mutations in ampG cause a deficiency in recycling of the peptidoglycan layer and lose 40% of their peptidoglycan per generation but remain viable. The sequence of the antisense RNA is shown in FIG. 5.

Antisense RNAs to lepB, ddlB, viaA and orf1 do not encode consensus ribosome loading sites. To determine if the chromosomal inserts within pJB37, pJB53, pJB57, and pJB59 could be translated into peptides, they were analyzed by computer for ribosome loading sites and open reading frames.

Plasmids pJB37, pJB53 and pJB57 do not have significant open reading frames or consensus ribosome loading sites relative to the inducible Bujard promoter. pJB59 does have an open reading frame relative to the Bujard promoter; however, no consensus ribosome loading site occurs in the antisense reading frames. The insert in pJB57 was shown to have a promoter which was active in an in vitro transcription/translation assay.

The antisense inserts in pJB37, pJB53, pJB57 and pJB59 do not encode lethal peptides. Sense plasmids were constructed to examine whether the deleterious effects on cell growth and viability could be caused by peptides produced by internal promoters in the inserts present in pJB37, pJB53, pJB57 and pJB59.

Sense orientation plasmids were generated by cutting antisense plasmids pJB57 and pJB59 with the enzymes BstBI and AccI which generates compatible ends. Each fragment mixture was then religated in the presence of AccI, which would recleave the plasmid if it religated in the "antisense" orientation but would not recognize the altered sites created by the fragment ligating in the "sense" orientation. Plasmids pCW57 and pCW59 contained the inserts from pJB57 and pJB59, respectively, in sense orientation.

To create pCW37 or pCW53, the inserts of pJB37 and pJB53 were amplified by PCR using the sequencing primers listed above. The PCR product was cut with HindIII and SmaI, filled in with Klenow and then cloned into the SmaI site of pLEX5BA, pCW37 and pCW53 contain the inserts from pJB37 and pJB53, respectively, in sense orientation. The orientation of all recombinants was verified by restriction analysis.

Cell proliferation for each strain was measured by diluting overnight cultures 1:10$^6$ into M9 medium. After growth to an $OD_{450}$ of 0.2, aliquots of each culture were plated on M9 agar without IPTG or M9 agar containing 1 mM IPTG. The results are shown in FIG. 6. Sense plasmids pCW37, pCW53, pCW57, and pCW59 had no measurable effect on cell growth or colony formation when induced with IPTG. In contrast, cells carrying pJB37 or pJB53 were unable to form colonies when plated with IPTG. Colony formation by cells carrying pJB57 was inhibited more than 100 fold. The colony formation of strains carrying pJB59 was inhibited more than 1000 fold. These results indicate that the inserts in pJB37, pJB53, pJB57 and pJB59 do not contain internal promoters expressing a lethal peptide in the sense orientation.

To test whether chromosomal inserts expressed proteins, 4 μg of CsCl purified plasmid templates was used in an in vitro transcription translation system for supercoiled templates (Promega, Madison, Wis.). The manufacturer's instructions were followed using 10 μCi $^{35}$S-methionine and 100 μM IPTG in a 50 μl reaction. Samples were precipitated with acetone and electrophoresed on 15% SDS PAGE. Bands were detected by exposure to a Molecular Dynamics phosphorimager and to film. No detectable peptide product was made from clones pJB37 or pJB59.

Kinetics of inhibition during exponential growth by antisense RNA. The kinetics of antisense inhibition was examined for strains carrying pJB37, pJB53, pJB57 or pJB59. Overnight cultures of each strain were diluted 1:20 into LB media containing 1 mM IPTG or LB media without IPTG. The $OD_{450}$ was then measured on the liquid cultures. FIG.

Figure 7:
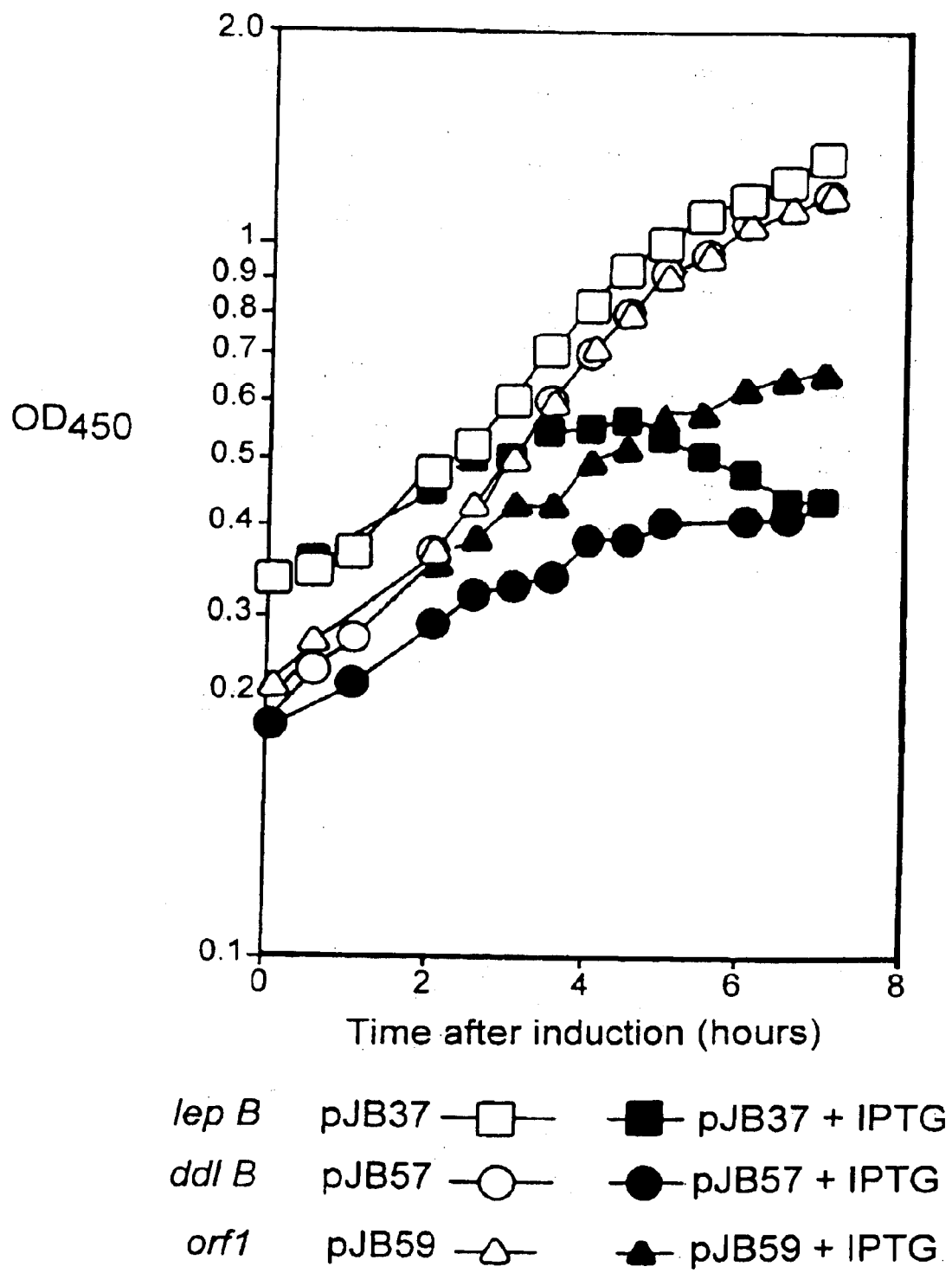
FIG. 7 is a graph showing growth curves of *E. coli* DH5α containing pJB37, pJB57 and pJB59 in liquid media in the presence and absence of IPTG.

7 shows the increase in $OD_{450}$ during exponential growth for pJB37, pJB57 and pJB59, with and without induction of antisense RNA. As seen in FIG. 7, transcriptional induction of antisense RNA did not have a significant effect on the increase in cell mass until about 3 hours after induction. Similar results were obtained for a strain carrying pJB53. After induction of antisense RNA expression, a few generations of cell division presumably are required in order to dilute endogenous gene product present at the initiation of induction. The cell mass for the strains expressing the lepB or viaA antisense RNAs (pJB37 and pJB53, respectively) began to decrease by about 4 hours, suggesting that cells had begun to lyse. Microscopic examination revealed that cells expressing lepB antisense RNA did lyse, whereas cells expressing viaA antisense RNA did not. The cell mass for strains carrying ddlB (pJB57) and orf1 (pJB59) stopped increasing after about 3 hours but did not decrease, suggesting that these cells did not lyse.

The $OD_{450}$ of strains carrying the sense constructs described above continued to increase, both in the presence and in the absence of IPTG, showing that induction of the sense RNA had no effect on bacterial proliferation.

Inhibition of viability by antisense RNA. The viability over time of the four strains expressing the antisense RNAs described above was also examined. Overnight cultures of each strain were diluted 1:100 into LB medium containing 1 mM IPTG. Aliquots of each culture were plated on LB agar containing ampicillin at intervals thereafter to determine CFUs/ml.

Figure 8:
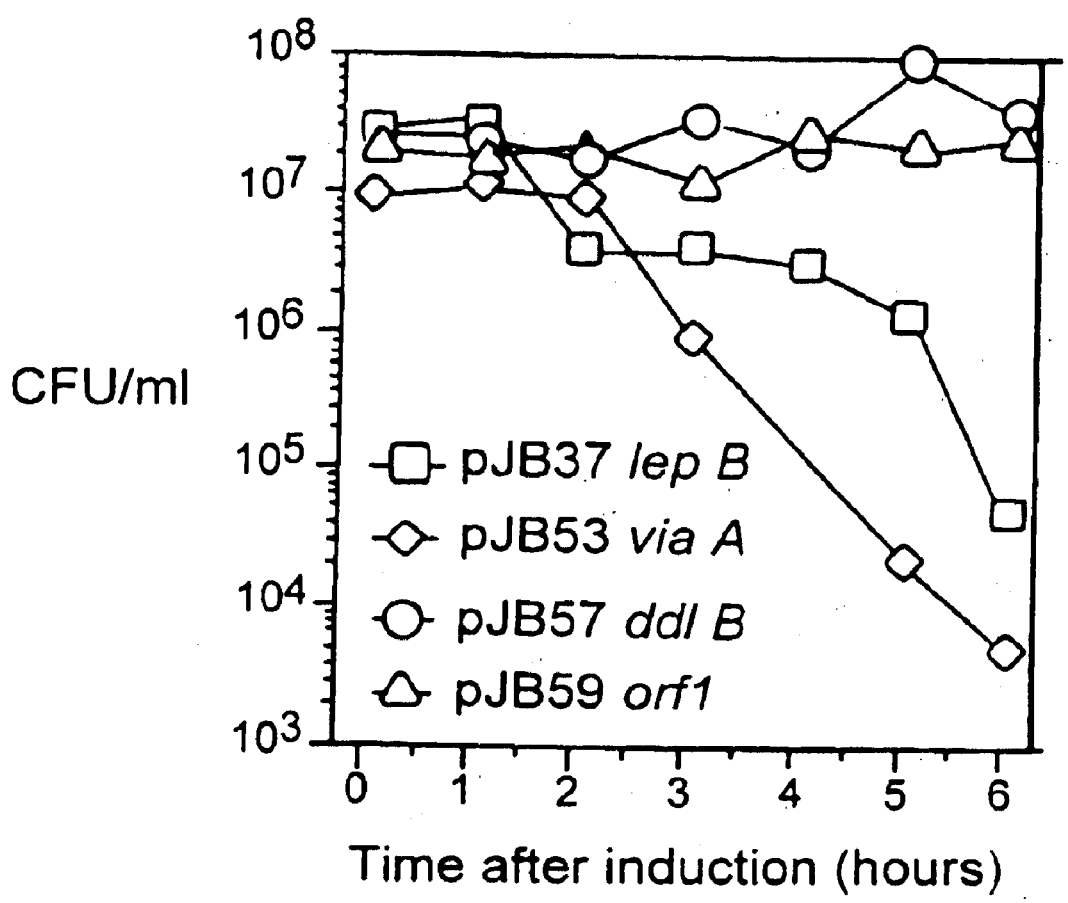
FIG. 8 is a graph showing the viability of DH5α strains at various times after induction of antisense RNA expression. Strains contained the following plasmids: squares: pJB37; diamonds: pJB53; circles: pJB57; and triangles; pJB59.

Data for strains carrying plasmids pJB37, pJB53, pJB57 and pJB59 are shown in FIG. 8. The data show that 6 hours after induction, viability is reduced by about 3 logs for strains expressing lepB or viaA antisense RNA. The data also show that growth is inhibited but viability is not reduced when ddlB or orf1 antisense RNAs are expressed. Optical density for strains expressing ddlB or orf1 antisense RNA increased over the period of the experiment, suggesting that cell size increases but cell division is inhibited for these strains. The results suggest that lepB or viaA antisense RNA is bacteriocidal, whereas ddlB or orf1 antisense RNA is bacteriostatic.

Effect of different concentrations of transcriptional inducer. Experiments were carried out to determine the effect of different concentrations of the inducer IPTG on bacterial growth and viability with the two clones where antisense RNA is bacteriocidal. Overnight cultures were diluted 1:100 into LB media containing 0, 10, 100 500 or 1000 micro molar (µM) IPTG. At the time of induction and every 2 hours thereafter, aliquots were plated on LB/ampicillin agar to determine CFUs/ml.

Figure 9:
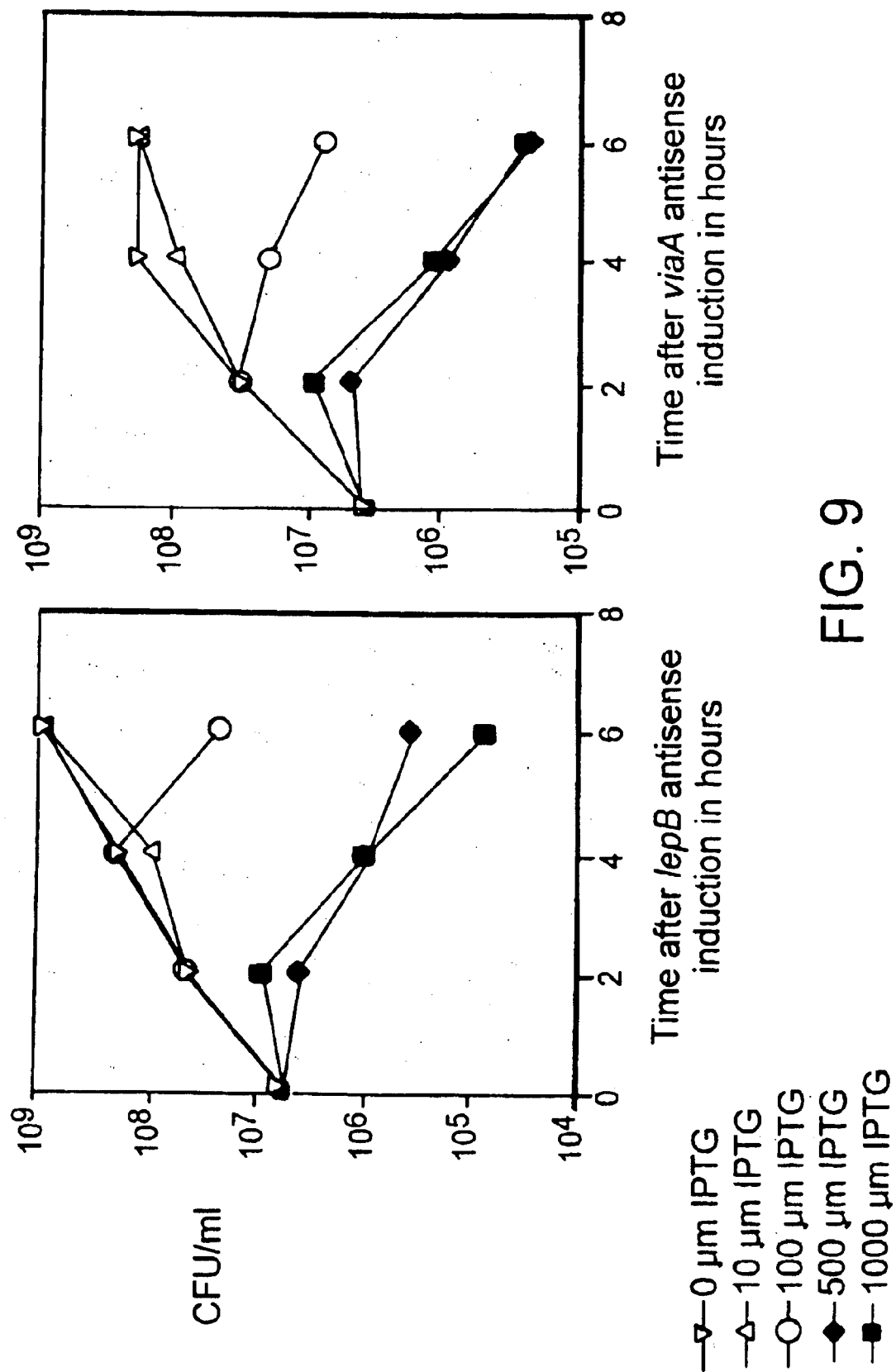
FIG. 9 is a graph showing the effect of varying concentrations of inducer on the viability of DH5α containing pJB37 (panel A) or pJB53 (panel B).

The results shown in FIG. 9 indicate that the antiproliferative effect of antisense to lepB or viaA is near maximal at 500 µm IPTG. Cell death occurred within 2 hours. A 2 fold increase to 1000 µm IPTG had little effect on the time of cell death. A 5 fold decrease in IPTG (100 µm) resulted in a longer period of survival (4 hours or more) before CFU began to decrease. However, cells did not survive overnight induction at 1000 µm IPTG, as shown in FIG. 6. Very low levels of IPTG (10 µm) had minimal effect on colony forming ability.

lepB antisense induction inhibits leader peptidase activity. The lepB gene encodes a leader peptidase that cleaves the leader sequence from preproteins such as maltose binding protein (MBP). Endogenous leader peptidase activity was examined in the presence of pJB37 antisense RNA, by measuring processing of pre-MBP (43.38 KD) to the mature 40.7 KD protein.

An overnight culture of pJB37/DH5α was diluted 1:100 in M9 media containing 0.2% casamino acids, 0.2% maltose, 100 µg/ml ampicillin. The diluted culture was split into 2 flasks, one containing 1 mM IPTG and the other containing no IPTG. Samples were taken at the time of the split and at hourly intervals thereafter. Chloramphenicol was added to each sample to a final concentration of 150 µg/ml. Samples were placed on ice, centrifuged, washed with M9 salts, and precipitated with cold 10% trichloroacetic acid (TCA). After centrifugation, the TCA precipitated material was resuspended in buffer (0.125 M Tris-HCL, pH 6.8, 0.1 M NaOH, 1% w/v SDS, 0.1% Phenol Red). The amount of protein in each precipitate was normalized to the different optical densities of the samples by using 0.1 ml of buffer per ml of culture having an $OD_{450}$ of 1.0. About 8 µl of each resuspended precipitate was mixed with an equal volume of 2× cracking buffer (100 mM Tris-Cl pH6.8, 200 mM DTT, 4% SDS, 0.2% bromophenol blue, 20% glycerol) and boiled for 10 minutes. Samples were electrophoresed on a 10% polyacrylamide-SDS gel as described in Sambrook et al., supra (1989).

Gel-separated proteins were electrophoretically transferred to a Protran nitrocellulose membrane (Schleicher & Schuell) and the membrane incubated with rabbit anti-MBP antibody diluted to 1:10,000. After washing, the membrane was incubated with a 1:10,000 dilution of goat anti-rabbit antibody conjugated to horseradish peroxidase (BioRad). Proteins were detected with a chemiluminescence kit (DuPont-NEN) and captured on autoradiographic film. The image was scanned using a Molecular Dynamics densitometer. The results showed that unprocessed MBP is detectable after induction of lepB antisense transcription with IPTG. No unprocessed MBP is detectable in untreated cells. The data demonstrate that lepB antisense RNA results in inhibition of the endogenous bacterial gene product.

Lethality of pJB59 antisense RNA requires inhibition of orf1. The polycistronic mRNA that encodes ampG in E. coli has an upstream ORF, termed orf1 herein: The antisense RNA made by pJB59 is complementary to orf1. In order to determine whether translational inhibition of orf1 or of ampG was the cause of the lethality of pJB59 antisense RNA, pJB59 was transformed into the ampG null strain, JRG58201. Jacobs, C., et al, EMBO J. 13:4684–4694 (1993). JRG58201 has a defect in the ampG gene but has no known defect in the orf1 gene.

Growth and viability of JRG58201 containing pJB59 was inhibited after IPTG induction. Thus, the anti-proliferative effect of the antisense RNA of pJB59 requires at least the inhibition of orf1 gene expression. Whether the antiproliferative effect of the ampG gene product is also involved cannot be determined from this experiment.

Effect of different antibiotic selectable markers on antisense inhibition of growth. The possibility that IPTG induction was sensitizing the cells to ampicillin was examined by transferring the inserts from plasmids pJB37, pJB53, pJB57 or pJB59 to the vector pAFΩ. Plasmid pAFΩ confers resistance to ampicillin, spectinomycin, and streptomycin. The resulting constructs were then tested for inhibition of bacterial growth using spectinomycin as the selectable marker rather than ampicillin.

pAFΩ was constructed by isolating the SmaI fragment containing Omega (Sp', St') of pHP45. Prentki and Kirsch, Gene 29:303–313 (1984). The omega fragment was then ligated into the filled-in ClaI site of pLEX5BA.

To generate pAF37, pAF53, pAF57, and pAF59, the inserts of pJB37, pJB53, pJB57, pJB59, respectively, were amplified by PCR. The PCR products of pJB37 and pJB353 were cut with HindIII, filled in with Klenow, and cut with EcoRI before ligation into EcoRI-SmaI cut pAFΩ. The PCR products of pJB57 and pJB59 were cut with PstI and EcoRI and ligated into identically cut pAFΩ. Ligation reactions were transformed into DH5α and ampicillin spectinomycin resistant transformants were selected. Generation of the correct constructs was verified by restriction analysis.

Overnight cultures of strains carrying plasmids pAF37, pAF57 or pAF59 were diluted 1:100 in LB medium containing spectinomycin. After growth to an $OD_{450}$ of 0.2, cells were plated on ampicillin, ampicillin with 1 mM IPTG, spectinomycin, or spectinomycin with 1 mM IPTG, and CFUs/ml of culture were determined. The results are shown in FIG. 10.

Figure 10:
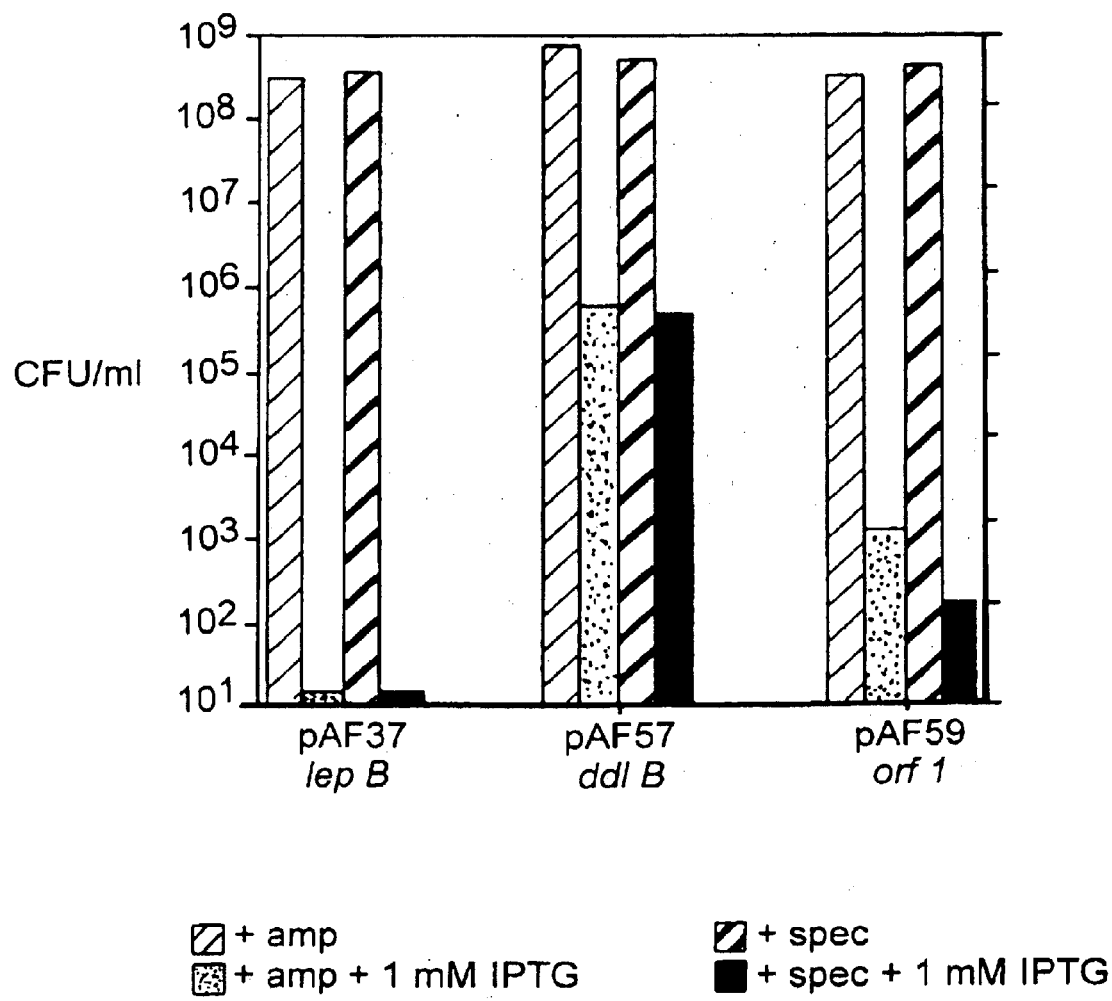
FIG. 10 is a bar graph comparing the effect of ampicillin or spectinomycin selection on viability of DH5α strains expressing lepB, ddlB, or orf1 antisense RNAs. Ampicillin selection (narrow stripes), ampicillin selection with 1 mM IPTG (gray), spectinomycin selection (wide stripes) and spectinomycin selection with 1 mM IPTG (solid).

FIG. 10 shows that induction of antisense nucleic acid under spectinomycin selection inhibits bacterial proliferation to the same extent as does antisense nucleic acid under ampicillin selection. Similar results were obtained for pAF53. These results suggest that the inhibition of bacterial proliferation observed with these constructs is not due to an effect on ampicillin resistance.

In order to examine the effectiveness of the antisense RNAs in a related species, *Salmonella typhimurium* was transformed with pJB37 or pJB53. The ampicillin-resistant transformants were plated on LB with or without 1 mM IPTG. Growth was greatly inhibited after induction of the antisense RNA, suggesting that sufficient complementarity existed between the antisense RNAs and *S. typhimurium* genes to inhibit production of proliferation gene products in this species as well as in *E. coli*.

The data described above indicate that antisense clones inhibit cell growth by producing an antisense RNA. Transcription of the cloned fragment must occur because IPTG induction is necessary to inhibit proliferation. None of the inserts are lethal in a sense orientation. Thus, any peptide possibly made by the insert in pJB57 is not responsible for lethality. No detectable peptide product is made from the antisense RNA of clones pJB37 or pJB59 in vitro. The pJB37 (lepB) antisense RNA was shown to decrease leader peptide processing activity.

Example 3

Identification of Proliferation Genes by Sense Inhibition

Four of the clones described in Example 1 inhibited bacterial proliferation and contained gene fragments in sense orientation. Plasmid pJB3 contained a fragment of the secA gene in sense orientation. Plasmid pJB60 contained a fragment of the ugpB gene in sense orientation. Plasmids pJB55 and pJB58 each contained a fragment in the sense orientation which expressed portions of genes having sequence homology to the *E. coli* fimF and fimD genes (located at 34 min on the *E. coli* map).

The insert in the secA dominant lethal clone, pJB3, was identified as an 836 bp PstI-HindIII fragment coding for yacA and the N-terminal 39 amino acids of the secA protein. The DNA sequence of the insert is shown in FIG. 11. SecA is an ATP-dependent translocase of secreted proteins located at the cytoplasmic face of the membrane. SecA protein regulates its own translation by binding to a site overlapping the ribosome binding site, which causes dissociation of a preformed 30S-tRNA-fMet-mRNA ternary complex. Since this site is located on the cloned fragment in pJB3, the sense RNA produced by pJB3 after induction could be binding and potentially sequestering most of the secA protein, resulting in a fatal deficiency in trans-membrane transport. Alternatively, the truncated secA peptide produced by pJB3 could be poisoning the membrane complex or binding the wild type mRNA, down regulating translation of secA.

An antisense RNA complementary to secA mRNA would also be expected to inhibit bacterial proliferation. The nucleotide sequence of such an antisense RNA is shown in FIG. 12.

The dominant lethal ugpB sense clone, pJB60, contains a 619 bp EcoRI-BamHI fragment which encodes the amino-terminal portion of the sn-glycerol-3-phosphate binding protein.

The insert in the dominant lethal clone, pJB58, is a BamHI-EcoRI fragment approximately 783 bp long. The plasmid insert contains two partial ORFs in a sense orientation. One partial ORF encodes the C-terminal portion of a protein which shows 59% similarity to FimD protein. The other partial ORF encodes the N-terminal portion of a protein with 56% similarity to FimF protein.

To the extent not already indicated, it will be understood by those of ordinary skill in the art that any one of the various specific embodiments herein described and illustrated may be further modified to incorporate features shown in other of the specific embodiments.

The foregoing detailed description has been provided for a better understanding of the invention only and no unnecessary limitation should be understood therefrom as some modifications will be apparent to those skilled in the art without deviating from the spirit and scope of the appended claims.

What is claimed is:

1. A method of screening for an antimicrobial agent, comprising the steps of:
   (a) providing a test compound, a microbial proliferation gene and a first and a second sample of a microorganism,
   wherein the microbial proliferation gene is identified by introducing an exogenous nucleic acid into the microorganism, the exogenous nucleic acid having substantial sequence identity to an endogenous microbial gene, wherein the exogenous nucleic acid is a random fragment or a random sequence, and, identifying the endogenous gene as a microbial proliferation gene by comparing the proliferation or viability of the microorganism when the exogenous nucleic acid is expressed in or introduced into the microorganism with the proliferation or viability of the microorganism when the exogenous nucleic acid is not present or not expressed,
   (b) introducing the microbial proliferation gene into the microorganism of the first sample;
   (c) contacting the test compound with the first sample and the second microorganism samples; and
   (d) determining the effect of the test compound on the first and the second microorganism samples, wherein the test compound is identified as an antimicrobial agent by comparing the effect of contacting the test compound to the first sample, where the exogenous nucleic acid is expressed or introduced, to the effect of contacting the test compound to the second sample, where the exogenous nucleic acid is not present, and the effect of the test compound on the contacted microorganism differs between the first and the second samples, thereby identifying the test compound as an antimicrobial agent.

2. The method of claim 1, wherein the effect of contacting the test compound with the microorganism is a change in the rate of proliferation of the contacted first microorganism sample as compared to the contacted second microorganism sample, thereby identifying the test compound as an antiproliferative antimicrobial agent.

3. The method of claim 1, wherein the effect of contacting the test compound with the microorganism is a microbiostatic effect on the contacted first microorganism sample as compared to the contacted second microorganism sample, thereby identifying the test compound as a microbiostatic antimicrobial agent.

4. The method of claim 1, wherein the effect of contacting the test compound with the microorganism is a microbiocidal effect on the contacted first microorganism as compared to the contacted second microorganism sample, thereby identifying the test compound as a microbiocidal antimicrobial agent.

5. The method of claim 1, wherein the effect of contacting the test compound with the first microorganism sample as compared to the second microorganism sample is a change in the rate of transcription or amount of a transcription product of the microbial proliferation gene in the first microorganism sample.

6. The method of claim 1, wherein the effect of contacting the antimicrobial agent with the microorganism is a change in the rate of translation or amount of a translation product of the microbial proliferation gene.

7. The method of claim wherein the translation product is a polypeptide.

8. The method of claim 1, wherein the effect of contacting the test compound with the microorganism is a change in the activity of a translation product of the microbial proliferation gene.

9. The method of claim 1, wherein the effect of contacting the test compound with the microorganism is a change in metabolism of the contacted microorganism.

10. The method of claim 1, wherein the effect of contacting the test compound with the microorganism is a change in viability of the contacted microorganism.

11. The method of claim 1, wherein an effect of the test compound is determined indirectly.

12. The method of claim 11, wherein an effect of the test compound is determined by a protein activity assay.

13. The method of claim 12, wherein the effect of the test compound agent is determined by an enzyme assay.

14. The method of claim 11, wherein the effect of the test compound is determined by an immunoassay.

15. The method of claim 1, wherein the effect of contacting the test compound with the microorganism is a change in the rate of proliferation, metabolism or viability of the contacted first microorganism sample as compared to the contacted second microorganism sample, thereby identifying the test compound as an antibiotic.

16. The method of claim 1, wherein introducing microbial proliferation gene into the microorganism of the first sample results in an increased level of expression of the transcription or translation product of the gene, thereby requiring contacting more test compound to the first sample than to the second sample to have the same effect on the microorganism.

17. The method of claim 1, wherein introducing the microbial proliferation gene into the microorganism of the first sample results in an decreased level of expression or activity of the translation product of an endogenous microbial proliferation gene, thereby requiring contacting less test compound to the first sample than to the second sample to have the same effect on the microorganism.

18. The method of claim 17, wherein the microbial proliferation gene is operably linked to a transcriptional regulatory element effective for controlling expression of the exogenous nucleic acid.

19. The method of claim 18, wherein the transcriptional regulatory element effective for controlling expression of the microbial proliferation gene is an inducible regulatory sequence.

20. The method of claim 19, wherein the inducible regulatory sequence that controls expression of the microbial proliferation gene is a promoter induced in response to a chemical inducer.

21. The method of claim 20, wherein chemical inducer comprises isopropyl-beta-D-thiogalactopyranoside, tetracycline or tryptophan.

22. The method of claim 19, wherein the inducible regulatory sequence that controls expression of the microbial proliferation gene is a promoter induced in response to environmental changes.

23. The method of claim 18, wherein the microbial proliferation gene is operably linked in an antisense orientation to the transcriptional regulatory element.

24. The method of claim 18, wherein the microbial proliferation gene is operably linked in a sense orientation to the transcriptional regulatory element.

25. The method of claim 1, wherein introducing the microbial proliferation gene into the microorganism of the first sample results in an decreased level of expression of the transcription product of an endogenous microbial proliferation gene, thereby requiring contacting less test compound to the first sample than to the second sample to have the same effect on the microorganism.

26. The method of claim 25, wherein the microbial proliferation gene is operably linked to a transcriptional regulatory element effective for controlling expression of the exogenous nucleic acid.

27. The method of claim 26, wherein the transcriptional regulatory element effective for controlling expression of the microbial proliferation gene is an inducible regulatory sequence.

28. The method of claim 27, wherein the inducible regulatory sequence that controls expression of the microbial proliferation gene is a promoter induced in response to a chemical inducer.

29. The method of claim 28, wherein chemical inducer comprises isopropyl-beta-D-thiogalactopyranoside, tetracycline or tryptophan.

30. The method of claim 27, wherein the inducible regulatory sequence that controls expression of the microbial proliferation gene is a promoter induced in response to environmental changes.

31. The method of claim 26, wherein the microbial proliferation gene is operably linked in an antisense orientation to the transcriptional regulatory element.

32. The method of claim 26, wherein the microbial proliferation gene is operably linked in a sense orientation to the transcriptional regulatory element.

33. The method of claim 1, wherein the microbial proliferation gene is endogenous to the microorganism.

34. The method of claim 1, wherein the microbial proliferation gene is a bacterial proliferation gene.

35. The method of claim 34, wherein the bacterial proliferation gene has substantial sequence identity to the *E. coli* viaA gene.

36. The method of claim 34, wherein the bacterial proliferation gene has substantial sequence identity to the *E. coli* orfl gene.

37. The method of claim 34, wherein the bacterial proliferation gene has substantial sequence identity to the *E. coli* lepB gene.

38. The method of claim 34, wherein the bacterial gene has substantial sequence identity to the *E. coli* ugpB gene.

39. The method of claim 34, wherein the bacterial proliferation gene has substantial sequence identity to the *E. coli* ddlB gene.

40. The method of claim 34, wherein the bacterial proliferation gene has substantial sequence identity to the *E. coli* secA gene.

41. The method of claim 34, wherein the bacterial proliferation gene has substantial sequence identity to a gene having sequence identity to *E. coli* fimF or fimD.

42. The method of claim 1, wherein the microorganism is a pathogen.

43. The method of claim 1, wherein the microorganism is a bacterium.

44. The method of claim 43, wherein the bacterium is a pathogen.

45. The method of claim 43, wherein the bacterium is a gram-negative bacterium.

46. The method of claim 45, wherein the gram-negative bacterium is *Escherichia coli*.

47. The method of claim 45, wherein the bacterium is a gram-positive bacterium.

48. The method of claim 47, wherein the gram-positive bacterium is *Staphylococcus aureus*.

49. The method of claim 1, wherein the microorganism is a fungus.

50. The method of claim 1, wherein the microorganism is a yeast.

51. The method of claim 1, wherein the microorganism is an Archaebacteria.

52. The method of claim 42, wherein the microorganism is a human pathogen.

53. The method of claim 42, wherein the microorganism is an animal pathogen.

54. The method of claim 42, wherein the microorganism is a plant pathogen.

55. The method of claim 1, wherein the exogenous nucleic acid is operably linked to a transcriptional regulatory element effective for controlling expression of the exogenous nucleic acid.

56. The method of claim 55, wherein the transcriptional regulatory element effective for controlling expression of the exogenous nucleic acid is an inducible regulatory sequence.

57. The method of claim 56, wherein the inducible regulatory sequence that controls expression of the exogenous nucleic acid is a promoter induced in response to a chemical inducer.

58. The method of claim 57, wherein chemical inducer comprises isopropyl-beta-D-thiogalactopyranoside, tetracycline or tryptophan.

59. The method of claim 56, wherein the inducible regulatory sequence that controls expression of the exogenous nucleic acid is a promoter induced in response to environmental changes.

60. The method of claim 55, wherein the exogenous nucleic acid is operably linked in an antisense orientation to the transcriptional regulatory element.

61. The method of claim 55, wherein the exogenous nucleic acid is operably linked in a sense orientation to the transcriptional regulatory element.

62. The method of claim 1, wherein the exogenous nucleic acid further comprises a vector.

63. The method of claim 62, wherein the vector is a plasmid or a phage vector.

64. The method of claim 1, wherein the exogenous nucleic acid is from about 10 to about 5,000 nucleotides in length.

65. The method of claim 64, wherein the exogenous nucleic acid is from about 15 to about 1,500 nucleotides in length.

66. The method of claim 1, wherein the exogenous nucleic acid is obtained from a nucleic acid selected from the group consisting of chromosomal DNA, episomal genomic DNA, RNA, cDNA and synthetic DNA.

67. The method of claim 1, wherein the test compound comprises a combinatorial library.

68. The method of claim 1, wherein the test compound comprises an inorganic compound.

69. The method of claim 1, wherein the test compound comprises an organic compound.

70. The method of claim 1, wherein the test compound comprises a peptidomimetic.

71. The method of claim 1, wherein the test compound comprises a polypeptide or a peptide.

72. The method of claim 1, wherein the test compound comprises an oligonucleotide or a polynucleotide.

73. The method of claim 1, wherein determining the effect of the test compound on the microorganism comprises comparative or replica plating of the microorganism.

74. The method of claim 1, wherein determining the effect of the test compound on the microorganism comprises measuring respiratory activity.

75. The method of claim 1, wherein determining the effect of the test compound on the microorganism comprises measuring colony-forming units, light scattering or optical density, the number of organisms in a particle counter, the fluorescence of cell cultures or of individual cells after addition of fluorescent dyes, the incorporation of precursors to macromolecules or the uptake of metabolites.

76. The method of claim 1, wherein the microorganism is a viable cell.

77. The method of claim 1, wherein the microorganism is a crude cell lysate.

78. The method of claim 1, wherein the test compound targets a transcription product of the microbial proliferation gene.

79. The method of claim 78, wherein the test compound selectively binds to the transcription product.

80. The method of claim 1, wherein the test compound targets a translation product of the microbial proliferation gene.

81. The method of claim 80, wherein the translation product is a polypeptide.

82. The method of claim 80, wherein the test compound selectively binds to the translation product.

83. A method of screening for antibacterial agents, comprising the steps of:
(a) providing a test compound, a microbial proliferation gene and a first and a second sample of a bacterium,
wherein the bacterial proliferation gene is identified by introducing an exogenous nucleic acid into the bacterium, the exogenous nucleic acid having substantial sequence identity to an endogenous bacterial gene, wherein the exogenous nucleic acid is a random fragment or a random sequence, and, identifying the endogenous gene as a bacterial proliferation gene by comparing the proliferation or viability of the bacterium when the exogenous nucleic acid is expressed in or introduced into the bacterium with the proliferation or viability of the bacterium when the exogenous nucleic acid is not present or not expressed,
(b) introducing the bacterial proliferation gene into the bacterium of the first sample;
(c) contacting the test compound with the first sample and the second bacterium samples; and
(d) determining the effect of the test compound on the first and the second bacterial samples, wherein the test compound is identified as an anti-proliferative antibacterial agent by comparing the effect of contacting the test compound to the first sample, where the exogenous nucleic acid is expressed or introduced, to the effect of contacting the test compound to the second sample, where the exogenous nucleic acid is not present, and the effect of the test compound on the contacted bacterium differs between the first and the second samples, thereby identifying the test compound as an anti-bacterial agent.

84. A method of screening for an antimicrobial agent, comprising the steps of:
(a) providing a test compound, a microbial proliferation gene and a first and a second sample of a first microorganism,
wherein the microbial proliferation gene is identified by introducing an exogenous nucleic acid into the first microorganism and the exogenous nucleic acid has substantial sequence identity to a microbial gene endogenous to the first microorganism and is a random fragment or a random sequence and is derived from a second microorganism, and, identifying the endogenous gene as a microbial proliferation gene by comparing the proliferation or viability of the first microorganism when the exogenous nucleic acid is expressed in or introduced with the proliferation or viability of the first microorganism when the exogenous nucleic acid is not present or not expressed,
(b) introducing the microbial proliferation gene into the first microorganism of the first sample;
(c) contacting the test compound with the first sample and the second microorganism samples; and
(d) determining the effect of the test compound on the first and the second microorganism samples, wherein the test compound is identified as an antimicrobial agent by comparing the effect of contacting the test compound to the first sample, where the exogenous nucleic acid is expressed or introduced, to the effect of contacting the test compound to the second sample, where the exogenous nucleic acid is not present or is not expressed, and the effect of the test compound on the contacted microorganism differs between the first and the second samples, thereby identifying the test compound as an antimicrobial agent.

85. A method of screening for antibacterial agents, comprising the steps of:
(a) providing a test compound, a microbial proliferation gene and a first and a second sample of a first bacterium,
wherein the bacterial proliferation gene is identified by introducing an exogenous nucleic acid into the first bacterium and the exogenous nucleic acid has substantial sequence identity to a bacterial gene endogenous to the first bacterium and the exogenous nucleic acid is a random fragment or a random sequence and is derived from a second bacterium, and, identifying the endogenous gene as a bacterial proliferation gene by comparing the proliferation or viability of the first bacterium when the exogenous nucleic acid is expressed in or introduced with the proliferation or viability of the first bacterium when the exogenous nucleic acid is not present or not expressed,
(b) introducing the bacterial proliferation gene into the first bacterium of the first sample;
(c) contacting the test compound with the first sample and the second bacterium samples; and
(d) determining the effect of the test compound on the first and the second bacterial samples, wherein the test compound is identified as an anti-proliferative antibacterial agent by comparing the effect of contacting the test compound to the first sample, where the exogenous nucleic acid is expressed or introduced, to the effect of contacting the test compound to the second sample, where the exogenous nucleic acid is not present or is not expressed, and the effect of the test compound on the contacted bacterium differs between the first and the second samples, thereby identifying the test compound as an anti-bacterial agent.

86. A method of screening for an antimicrobial agent, comprising the steps of:
   (a) providing a test compound, a microbial gene essential for viability or growth and a first and a second sample of a microorganism,
   wherein the microbial gene essential for viability or growth is identified by introducing an exogenous nucleic acid into the microorganism and the exogenous nucleic acid is a random fragment or a random sequence, and, identifying the endogenous gene as a gene essential for viability or growth by comparing the proliferation or viability of the microorganism when the exogenous nucleic acid is expressed in or introduced with the proliferation or viability of the microorganism essential for viability or growth when the exogenous nucleic acid is not present or not expressed,
   (b) introducing the microbial gene into the microorganism of the first sample;
   (c) contacting the test compound with the first sample and the second microorganism samples; and
   (d) determining the effect of the test compound on the first and the second microorganism samples, wherein the test compound is identified as an antimicrobial agent by comparing the effect of contacting the test compound to the first sample, where the exogenous nucleic acid is expressed or introduced, to the effect of contacting the test compound to the second sample, where the exogenous nucleic acid is not present or not expressed, and the effect of the test compound on the contacted microorganism differs between the first and the second samples, thereby identifying the test compound as an antimicrobial agent.

87. A method of screening for an anti-bacterial agent, comprising the steps of:
   (a) providing a test compound, a gene essential for viability or growth and a first and a second sample of a bacterium,
   wherein the gene essential for viability or growth is identified by introducing an exogenous nucleic acid into the bacterium and the exogenous nucleic acid is a random fragment or a random sequence, and, identifying the endogenous gene essential for viability or growth by comparing the proliferation or viability of the bacterium when the exogenous nucleic acid is expressed in or introduced with the proliferation or viability of the bacterium when the exogenous nucleic acid is not present or not expressed,
   (b) introducing the exogenous gene into the bacterium of the first sample;
   (c) contacting the test compound with the first sample and the second bacterial samples; and
   (d) determining the effect of the test compound on the first and the second comparing the effect of contacting the test compound to the first sample, where the exogenous nucleic acid is expressed or introduced, to the effect of contacting the test compound to the second sample, where the exogenous nucleic acid is not present or not expressed, and the effect of the test compound on the contacted bacterium differs between the first and the second samples, thereby identifying the test compound as an anti-bacterial agent.

88. A method of screening for an antimicrobial agent, comprising the steps of:
   (a) providing a test compound, a microbial proliferation gene and a first and a second sample of a first microorganism,
   wherein the microbial proliferation gene is identified by introducing an exogenous nucleic acid into the first microorganism and the exogenous nucleic acid has substantial sequence identity to a microbial gene endogenous to the first microorganism and is a random antisense fragment or a random antisense sequence, and, identifying the endogenous gene as a microbial proliferation gene by comparing the proliferation or viability of the first microorganism when the exogenous nucleic acid is expressed in or introduced with the proliferation or viability of the first microorganism or an equivalent microorganism when the exogenous nucleic acid is not present or not expressed,
   (b) introducing the microbial proliferation gene into the first microorganism of the first sample;
   c) contacting the test compound with the first sample and the second microorganism samples; and
   (d) determining the effect of the test compound on the first and the second microorganism samples, wherein the test compound is identified as an antimicrobial agent by comparing the effect of contacting the test compound to the first sample, where the exogenous nucleic acid is expressed or introduced, to the effect of contacting the test compound to the second sample, where the exogenous nucleic acid is not present or is not expressed, and the effect of the test compound on the contacted microorganism differs between the first and the second samples, thereby identifying the test compound as an antimicrobial agent.

* * * * *

SEQUENCE LISTING

```
<160> NUMBER OF SEQ ID NOS: 9

<210> SEQ ID NO 1
<211> LENGTH: 18
<212> TYPE: DNA
<213> ORGANISM: Artificial Sequence
<220> FEATURE:
<223> OTHER INFORMATION: Primer 5' to 3'

<400> SEQUENCE: 1
tgttttatca gaccgctt                                                    18
```

-continued

<210> SEQ ID NO 2
<211> LENGTH: 18
<212> TYPE: DNA
<213> ORGANISM: Artificial Sequence
<220> FEATURE:
<223> OTHER INFORMATION: Primer 5' to 3'

<400> SEQUENCE: 2
acaatttcac acagcctc                                                    18

<210> SEQ ID NO 3
<211> LENGTH: 546
<212> TYPE: RNA
<213> ORGANISM: Escherichia coli lepB

<400> SEQUENCE: 3
cugcagaagc agaaagaagg uaagaaacgc augaagcaga ucgguaacgu cgagcugccg      60
caggaagcgu uccucgccau ucugcacguc ggcaaagaca acaaauaacc cuuaggaguu     120
ggcauggcga auauguuugc ccugauucug ugauugcca cacugugac gggcauuuua       180 uggugcugg auaaauucuu uuucgcaccu aaacggcggg aacgucaggc agcggcgcag      240
gcggcucggg acucacugga uaaagcaacg uugaaaaagg uugcgccgaa gccuggcugg    300
cuggaaaccg gugcuucugu uuuccgguua cuggcuaucg uauugauugu gcguucguuu    360
auuuaugaac cguuccagau cccgucaggu ucgaugaugc cgacucuguu aauuggugau    420
uuuauucugg uagagaaguu ugcuuauggc auuaaagauc cuaucuacca gaaaacgcug    480
aucgaaaacg gucauccgaa acgcggcgau aucguggucu uuaaauaucc ggaagaucca    540
aagcuu                                                               546

<210> SEQ ID NO 4
<211> LENGTH: 714
<212> TYPE: RNA
<213> ORGANISM: Escherichia coli viaA

<400> SEQUENCE: 4
cugcaggcug aggauuugcc cuuacaaaug caacaacgac auggauuaca cacccucau      60 aaacaaaggg caaucaccug aucuaagcuc uuaccauga cagugauagg uuaugccuuu     120
uacucgacuu uugcacugac ugaaaaggac aaauuaaugu uaaaaaagau acuuuuacug    180
gcucugcuuc cugcaaucgc cuucgcagag gaacuuccug cuccaguaaa agcgauugaa    240
aaacagggca uuacaaucau caaaacauuc gaugccccg gaggaaugaa agguuaucuc    300
ggaaaguauc aggauauggg cgucaccauc uaccugacuc cagauggaa gcacgcuauc    360 ucugguuaca guacaacga aaaggugaaa accgaguacu acacacuuau cgaaaaagaa    420
auuuacgcac cagccggacg cgaaaugugg caacggaugg aacaauccca cuggcuccuc   480
gacgguaaaa aagaugcgcc ggucauuguc uacgcuucg ccgauccguu cugcccauau    540
uguaaacagu ucuggcagca ggcgcgcccg ugggugauu cugcaaagu gcaauuaaga    600 acauuguugg uuggguuau caagccagaa agcccggcga cagcagcggc aauucuugcc    660
uccaaagauc ccgcaaaaac cuggcaacaa uaugaagccu cuggugcaa gcuu           714

<210> SEQ ID NO 5
<211> LENGTH: 714
<212> TYPE: DNA
<213> ORGANISM: Escherichia coli viaA -continued

```
<400> SEQUENCE: 5
ctgcaggctg aggtgttgcc cttacaaatg caacaacgac atggattaca acaccctcat    60
aaacaaaggg caatcacctg atctaagctc ttacctatga cagtgatagg ttatgccttt   120
tactcgactt ttgcactgac tgaaaaggac aaattaatgt taaaaagat acttttactg    180 gctctgcttc ctgcaatcgc cttcgcagag gaacttcctg ctccagtaaa agcgattgaa   240
aaacagggca ttacaatcat caaaacattc gatgccccg gaggaatgaa aggttatctc    300
ggaaagtatc aggatatggg cgtcaccatc tacctgactc cagatggtaa gcacgctatc   360
tctggttaca tgtacaacga gaaaggtgaa aacctgagta acacacttat cgaaaaagaa   420
atttacgcac cagccggacg cgaaatgtgg caacggatgg aacaatccca ctggctcctc   480
gacggtaaaa aagatgcgcc ggtcattgtc tacgtcttcg ccgatccgtt ctgcccatat   540
tgtaaacagt tctggcagca ggcgcgcccg tgggtagatt ctggcaaagt gcaattaaga   600
acattgttgg ttggggttat caagccagaa agcccggcga cagcagcggc aattcttgcc   660
tccaaagatc ccgcaaaaac ctggcaacaa tatgaagcct ctggtggcaa gctt          714

<210> SEQ ID NO 6
<211> LENGTH: 1050
<212> TYPE: RNA
<213> ORGANISM: Escherichia coli ddlB

<400> SEQUENCE: 6
gaauucguac uaccaacugc gagaagcuca uaccugccug acgugccgcc aucggcacca    60
ggcuguggcu ggucauaccc ggugagguau uggcuuccag cagauaaaac uguccaucgc   120
uguccagcau aacgucaaua cgucccauc cuuugcaacc uaacgucguc caugcuuuca    180
gcacuaaugc cugcaaauug gccucuugug acgcuuccag accugcgggg cagaaauacu   240
gugucucauc agagagauac uucgccucau aaucauagaa gguuccggac gguugaauac   300
guauugacgg uaaaauuucu ucaccgagua ucgcaaccgu gaacuccggc ccacuuagcc   360
auuuuucaau caauacuucu ucaucgugcu gaaaugccaa ucuuaaugca ucuuguagag   420
cauuuucugc uacuacuuuu gacauuccca cacuggaacc uucgcggcuc ggcuuaacga   480
uaaccggcaa acccagagca gaaauuucug cuaacugcuu aucgcucagg ccuuuuucaa   540
acucugcgcg gguuaacgcu acccacggcg cgaccgguaa accggcaccu ugccauagaa   600
guuugcugcg uaguuuaucc auugaaagcg cagaugccau cacuccgcuu ccgguauaag   660
gcaagcccau cagcucgagc auccccugca gcguaccauc uucaccgccg cgaccgugua   720
gcgcgauaaa cacuuucuga agcccaucg acuucaguug cgucacgucg acuucuuucg   780
ggucgacagg auacgcguca uaccgccuu cacgcacucc ggcuaacacc gcugcgccag    840
aauucagaga acuucccgc ucagcggagg ucccacccaa caggaccgcg auuuuaucag    900
ucauguuguu cuuccuccgg aguuugcggc uucaguuuga uuucagcuaa gaacgggca    960 auuuuccaa uauuaccagc ccccugaacg agaaucaggu cguuaccggu uaauaccggu   1020
gccagcaucu cggcuacccg cgccggaucc                                    1050

<210> SEQ ID NO 7
<211> LENGTH: 451
<212> TYPE: RNA
<213> ORGANISM: Escherichia coli ampG

<400> SEQUENCE: 7
gaauucgugg augcuggugu ccugagacau aucagcgaug guaucgguca gcacacuguu    60
```

-continued

```
aaccgcaucg gcgauauuuu uguuggaggc cuggaacgca ccuucaacgu uguagcuggc      120
acgauaguuu uuggucauuu guugccauu cugcgcggua gcgaugaugg cgauauccgc      180
uuuggucgcg auguuguagc gcacguugcc cuggacacg ucagcauaca guuggcuaac      240
gaugauuugc agauuaaccg ggccauucgg accaaccaug uaccacgcg cggucaucug      300 uuuuuccagc acucuugca gcaggaaacg cagaucgcgg gaggcgguca gguaacgau       360 uugauuaucg cgggugacuu uugccagcgc cugaucgua cgcugaucgg caccauuaau      420
gcuuacggug acgcccauca ggcuuggauc c                                    451
```

<210> SEQ ID NO 8
<211> LENGTH: 836
<212> TYPE: DNA
<213> ORGANISM: Escherichia coli secA

<400> SEQUENCE: 8

```
ctgcaggctt taatgataag atttgtgcgc taaatacgtt tgaatatgat cgggatggca      60
ataacgtgag tggaatactg acgcgctggc gacagtttgg taaacgctac ttctggccgc     120
atctcttatt agggatggtt gcggcgagtt taggtttgcc tgcgctcagc aacgccgccg     180
aaccaaacgc gcccgcaaaa gcgacaaccc gcaaccacga gccttcagcc aaagttaact     240
ttggtcaatt ggccttgctg gaagcgaaca cacgccgccc gaattcgaac tattccgttg     300
attactggca tcaacatgcc attcgcacgg taatccgtca tctttctttc gcaatggcac     360
cgcaaacact gcccgttgct gaagaatctt tgcctcttca ggcgcaacat cttgcattac     420
tggatacgct cagcgcgctg ctgacccagg aaggcacgcc gtctgaaaag ggttatcgca     480
ttgattatgc gcatttacc ccacaagcaa aattcagcac gcccgtctgg ataagccagg     540
cgcaaggcat ccgtgctggc cctcaacgcc tcacctaaca acaataaacc tttacttcat     600
tttattaact ccgcaacgcg gggcgtttga gattttatta tgctaatcaa attgttaact     660
aaagttttcg gtagtcgtaa cgatcgcacc ctgcgccgga tgcgcaaagt ggtcaacatc     720
atcaatgcca tggaaccgga gatgaaaaa ctctccgacg aagaactgaa agggaaaacc     780
gcagagtttc gtgcacgtct ggaaaaaggc gaagtgctgg aaaatctgat cccgga         836
```

<210> SEQ ID NO 9
<211> LENGTH: 836
<212> TYPE: RNA
<213> ORGANISM: Escherichia coli secA

<400> SEQUENCE: 9

```
uccgggauca gauuuuccag cacuucgccu uuuuccagac gugcacgaaa cucugcgguu     60
uucccuuuca guucuucguc ggagaguuuu uccaucuccg guccauggc auugaugaug      120 uugaccacuu ugcgcauccg gcgcagggug cgaucguuac gacuaccgaa acuuuaguu      180 aacaauuuga uuagcauaau aaaaucucaa acgccccgcg uugcggaguu auaaaauga     240 aguaaagguu uauuguuguu aggugaggcg uugagggcca gcacggaugc cuugcgccug    300
gcuuauccag acgggcgugc ugaauuugc uguggggua aaaugcgcau aaucaaugcg      360
auaacccuuu ucagacggcg ugccuuccug ggucagcagc gcgcugagcg uaccaguaa     420 ugcaagaugu ugcgccugaa gaggcaaaga uucuucagca acgggcagug uuugcggugc    480
cauugcgaaa gaaagaugac ggauuaccgu gcgaauggca guugaugcc aguaaucaac     540 ggaauaguuc gaauucgggc ggcgugugu cgcuuccagc aaggccaauu gaccaaagu u    600
```

| | | | | | | |
|---|---|---|---|---|---|---|
| aacuuuggcu | gaaggcucgu | gguugcgggu | ugucgcuuuu | gcgggcgcgu | uugguucggc | 660 |
| ggcguugcug | agcgcaggca | aaccuaaacu | cgccgcaacc | aucccuaaua | agagaugcgg | 720 |
| ccagaaguag | cguuuaccaa | acugucgcca | gcgcgucagu | auuccacuca | cguuauugcc | 780 |
| aucccgauca | uauucaaacg | uauuuagcgc | acaaaucuua | ucauuaaagc | cugcag | 836 |